United States Patent [19]
Hiroi et al.

[11] Patent Number: 5,430,548
[45] Date of Patent: Jul. 4, 1995

[54] METHOD AND APPARATUS FOR PATTERN DETECTION

[75] Inventors: Takashi Hiroi, Yokohama; Hitoshi Kubota, Fujisawa; Shunji Maeda; Hiroshi Makihira, both of Yokohama; Mitsunobu Isobe, Machida, all of Japan

[73] Assignee: Hitachi, Ltd., Tokyo, Japan

[21] Appl. No.: 12,468

[22] Filed: Feb. 2, 1993

[30] Foreign Application Priority Data

Feb. 6, 1992 [JP] Japan .................. 4-020966

[51] Int. Cl.6 ............. G01N 21/01; G01N 21/15
[52] U.S. Cl. ................... 356/394; 356/357; 356/350; 250/548
[58] Field of Search ............ 356/401, 374, 363, 361, 356/400, 394, 350, 357, 349, 351, 395–398; 250/548, 571, 561

[56] References Cited

U.S. PATENT DOCUMENTS

| 3,683,679 | 9/1972 | Brenden et al. | 367/8 |
| 3,909,602 | 9/1975 | Micka | 356/394 |
| 4,692,690 | 9/1987 | Hara et al. | 356/394 |
| 4,777,641 | 10/1988 | Inagaki et al. | 250/491.1 |
| 4,862,008 | 9/1989 | Oshida et al. | 356/401 |
| 4,906,852 | 3/1990 | Nakata et al. | 356/401 |
| 4,952,058 | 8/1990 | Noguchi et al. | 356/394 |
| 5,028,802 | 7/1991 | Webb et al. | 250/571 |
| 5,048,967 | 9/1991 | Suzuki et al. | 356/394 |
| 5,075,562 | 12/1991 | Greivenkamp, Jr. et al. | 356/374 |
| 5,098,191 | 3/1992 | Noguchi et al. | 356/394 |
| 5,227,862 | 7/1993 | Oshida et al. | 356/367 |

FOREIGN PATENT DOCUMENTS

| 0039811 | 12/1982 | Japan . |
| 0200042 | 8/1988 | Japan . |
| 0024539 | 1/1990 | Japan . |
| 0111336 | 4/1992 | Japan . |

Primary Examiner—Robert P. Limanek
Assistant Examiner—Alexander Oscar Williams
Attorney, Agent, or Firm—Antonelli, Terry, Stout & Kraus

[57] ABSTRACT

The inventive pattern detection method and apparatus produce, from an optical image of a pattern in attention and an optical image of a pattern which should be identical to the pattern in attention, an optical image by merging the images, with a relative phase shift being imposed, and pattern information is detected or observed in the merged optical image or a signal produced from the optical image through the conversion with an opto-electric transducer means.

7 Claims, 20 Drawing Sheets

FIG. 1A
STORED PATTERN
FIG. 1B
DETECTED PATTERN
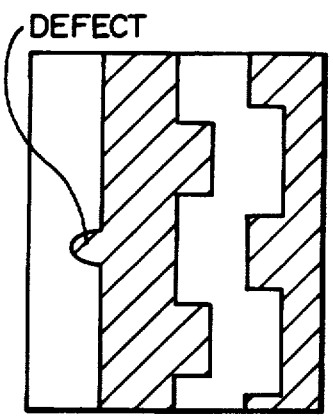
DEFECT
FIG. 1C
PATTERN DIFFERENCE
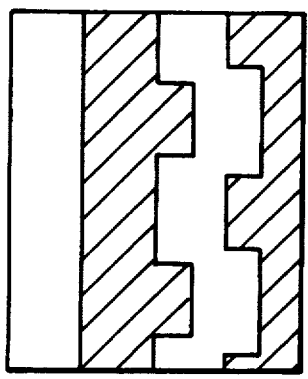
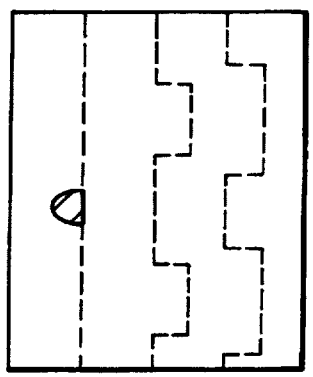
FIG. 2A
WAFER PATTERN
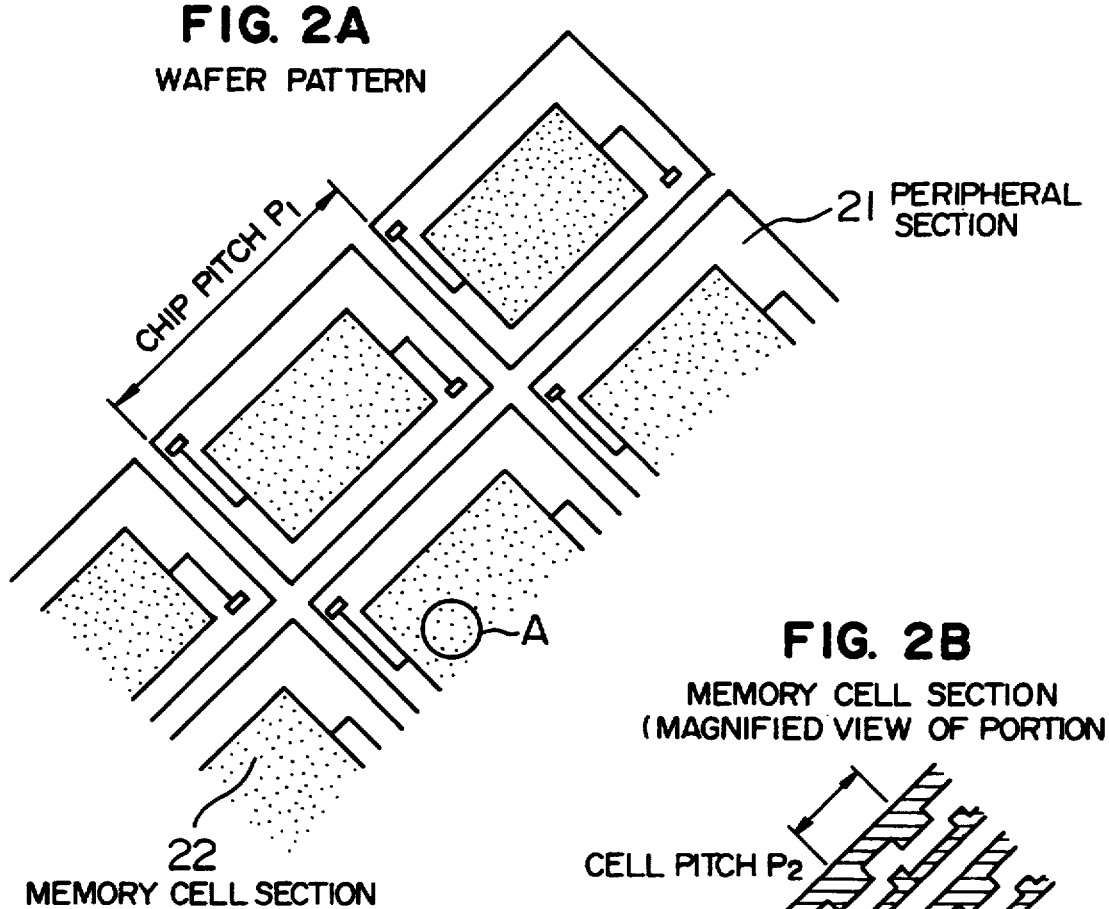
CHIP PITCH P₁
21 PERIPHERAL SECTION
A
22 MEMORY CELL SECTION
FIG. 2B
MEMORY CELL SECTION (MAGNIFIED VIEW OF PORTION A)
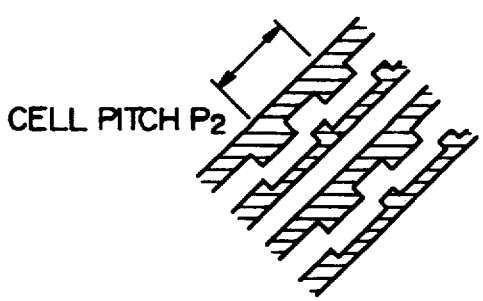
CELL PITCH P₂

TOP VIEW OF WAFER

ROTATION BETWEEN ROTATIONAL ANGLE AND DETECTED LIGHT INTENSITY

RELATION BETWEEN SHEAR VALUE
AND DETECTED LIGHT INTENSITY

FIG. 8A
ORDINARY WAY DETECTION PATTERN
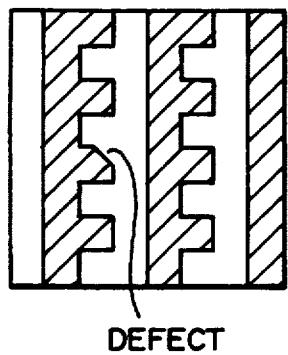
DEFECT
FIG. 8B
X DIRECTION SHEAR DETECTION PATTERN
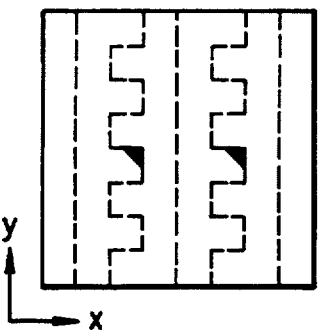
FIG. 8C
Y DIRECTION SHEAR DETECTION PATTERN
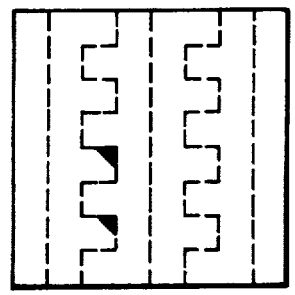
FIG. 9A
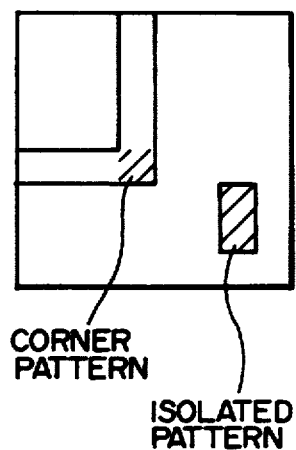
CORNER PATTERN
ISOLATED PATTERN
FIG. 9B
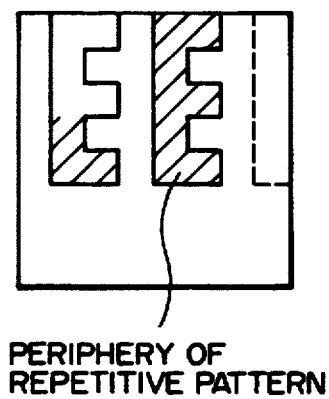
PERIPHERY OF REPETITIVE PATTERN
FIG. 9C
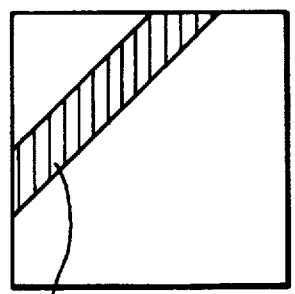
OBLIQUE PATTERN
 HATCHED PORTION INDICATES EXCEPTIONAL PATTERNS

STRUCTURE OF FRESNEL PLATE

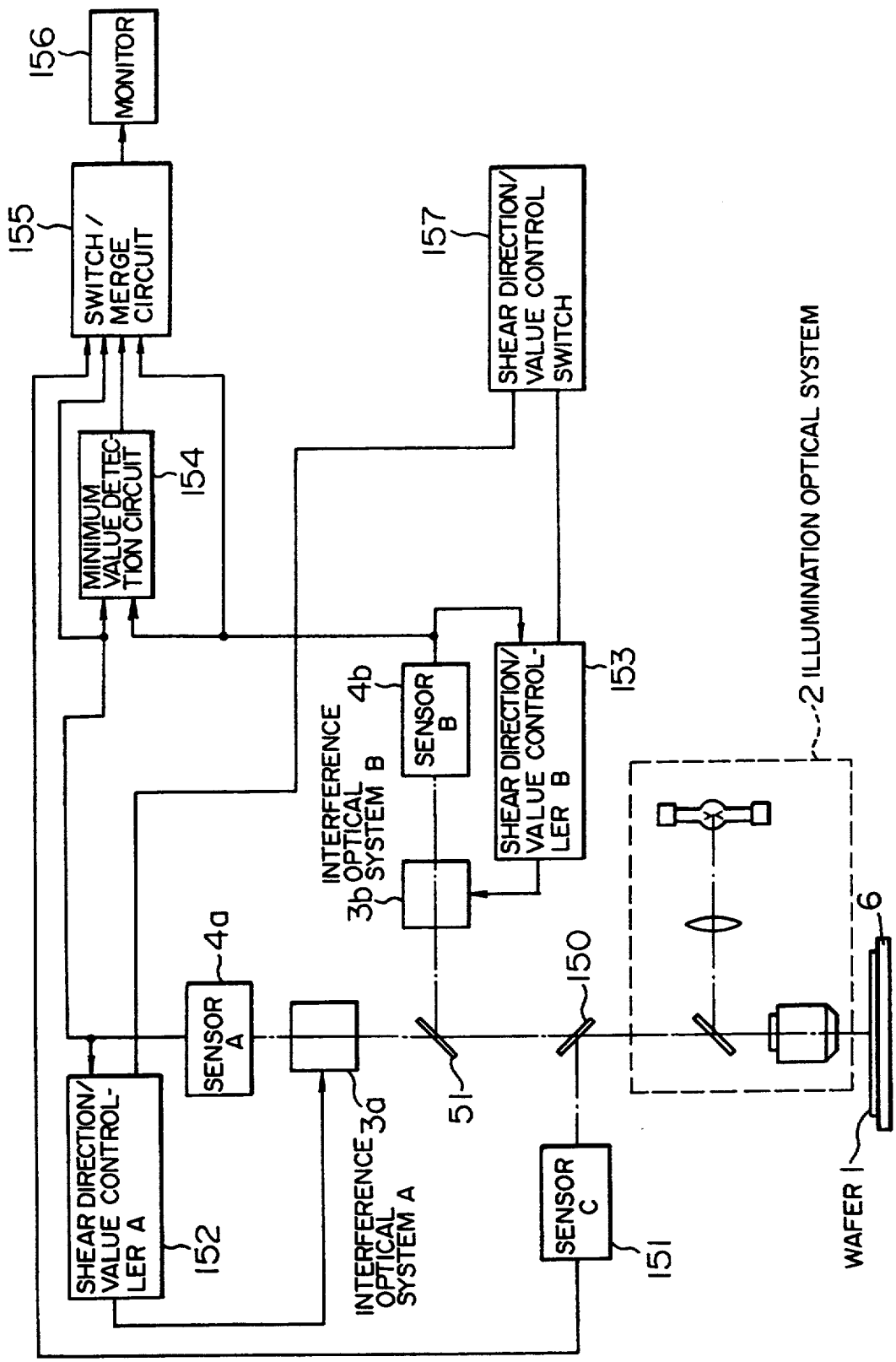

PATTERN OF ONLY x DIRECTION

PATTERN OF ONLY y DIRECTION

METHOD AND APPARATUS FOR PATTERN DETECTION

BACKGROUND OF THE INVENTION

This invention relates to a method and apparatus for detecting an optical image of pattern information, such as a defect, of an object having a one or two-dimensional array of repetitive patterns including a pattern under inspection and a pattern which should be identical to the pattern under inspection, e.g., LSI wafers, masks of TFTs and reticles, or multi-layer thin or thick film wiring boards.

A first prior art described in Japanese Patent Publication No. 62-39811 is designed such that an optical image of a pattern on a semiconductor chip is received by an opto-electric transducer means, a digital image signal produced by the opto-electric transducer means is stored as a stored pattern as shown in FIG. 1A in a memory, an optical image of a pattern on the adjacent chip is received by the opto-electric transducer means, and a digital image signal produced by the opto-electric transducer means as the second detected pattern as shown in FIG. 1B is compared with the stored digital image signal thereby to detect a defect of pattern based on their difference as shown in FIG. 1C. Namely, in this prior art, the detection of a pattern defect is based on the comparison process between a digital image signal produced for a pattern by the opto-electric transducer means and a reference digital image signal.

A second prior art described in Japanese Patent Unexamined Publications Nos. 2-24539 and 4-111336 is designed such that a light beam produced by a light source (e.g., laser source) is split into two beams by means of a half mirror or the like, the resulting beams are projected onto two object sections, transmitted or reflected beams from the objects are merged with the same half mirror, and the output beam of this half mirror is detected with a sensor. The light paths for the two objects are set to have distances different by $\lambda/2$ or $\lambda \times (n+\frac{1}{2})$ (where n=0, 1, 2, ... ) so that optical interference is induced. The sensor output is subjected to differential detection for two patterns so that the detected signal has a zero level when both objects are the same pattern or it has a significant level if these patterns are different, i.e., the signal is predetermined at a defective portion.

In regard to the first prior art, when it is intended to detect a smaller defect, the digital image signal produced by the opto-electric transducer means must have a finer pixel size and, on the other hand, the detection speed is proportional to the square of the pixel size. The detection speed is determined from the number which is the detection area per pixel multiplied by the clock frequency of sensor per pixel multiplied by the number of parallel processing. Using the above expression, if the pixel size becomes smaller, the area of pixel becomes smaller in proportion to the square of the pixel size and the detection speed also falls in proportion to the square of the pixel size. Namely, this prior art which bases the judgement of defect on the detected digital image does not consider the performance of pattern detection in search of small defects without incurring the reduction of pattern detection speed.

In regard to the second prior art, it is necessary to set the difference of distances of the light paths passing through the two objects to $\lambda/2$ or $\lambda \times (n+\frac{1}{2})$ accurately. For example, when the optical system intended for the reflective detection with a wavelength $\lambda$ of 633 mm has a 30 nm stability of distance of the two light paths, the light path distances may have errors as large as $\lambda/10$, and the detected light caused by these distance errors can possibly be judged erroneously as a defect. It is conceivably very difficult to attain a stability of 30 nm or less for the optical system with complete separate object stages or light paths because of the vibration of the object stages and the stability of air. The following explains in more detail.

The light intensity $u_1$ and $u_2$ reflected by the objects are expressed by the following expressions.

$$u_1 = A_1 \times \exp\{i(w \times t + \delta_1)\} \quad (1)$$

$$u_2 = A_2 \times \exp\{i(w \times t + \delta_2)\} \quad (2)$$

where $A_1$ and $A_2$ are amplitudes of the light, t is the time, $\omega$ is the frequency of the light, and $\delta_1$ and $\delta_2$ are phases.

In case the two light intensity $u_1$ and $u_2$ have a sufficient interference characteristics, and the two objects have an equal reflectivity and are the same pattern, the strength of interference I is given by the following expression.

$$I = 2 \times A\{1 + \cos(\delta_1 - \delta_2)\} \quad (3)$$

where $A = A_1 = A_2$.

If the distances to the two object stages have an error of $\lambda/10$ (e.g., for $\lambda = 500$ nm, the error is 50 nm), the term $\delta_1 - \delta_2$ is evaluated to be $\pi \pm \pi/5$ and then the detected light intensity I is evaluated to be $0.19A_2$ which is 4.7% of the maximum value $4A_2$. This light intensity can possibly be judged erroneously as a defect. As described above, the second prior art does not sufficiently consider the stability of the optical system in putting the technology into practice.

SUMMARY OF THE INVENTION

This invention is intended to overcome the foregoing prior art deficiencies, and its object is to provide a method and apparatus for pattern detection capable of detecting a small difference of patterns, such as a defect of pattern, stably and without deteriorating the detection speed through the direct detection of a pattern difference as an image signal based on the optical interference (optical split, phase shift and merge).

The pattern detection method is designed to merge an optical image of a pattern in consideration and an optical image of a pattern which is expected to be identical to the pattern in consideration into a signal of optical image with relatively shifted phase, observe or detect the signal of optical image by an opto-electric transducer means, and extract pattern information, such as defects, from the signal of optical image. The inventive pattern detection method is designed to split an optical image of a repetitive pattern into multiple images, merge an optical image of a pattern in consideration and an optical image of a pattern which is expected to be identical to the pattern in consideration into a signal of optical image with relatively shifted phase, observe or detect the signal of optical image by an opto-electric transducer means, and extract pattern information, such as defects, from the signal of optical image.

The inventive pattern detection method comprises a first detection step of splitting an optical image of a first repetitive pattern into multiple images and producing with an opto-electric transducer means a signal of an optical image by merging the images, with a relative phase shift being imposed depending on the property of repetitiveness, a second detection step of splitting an optical image of a second repetitive pattern having an interval different from that of the first pattern into multiple images and producing with the opto-electric transducer means a signal of an optical image by merging the images, with a relative phase shift being imposed depending on the property of repetitiveness, and a third detection step of detecting pattern information based on the signals produced in the first and second steps.

The inventive pattern detection apparatus comprises an illumination optical system which illuminates with a coherent or partially coherent light a pattern under inspection and a pattern which should be identical to the pattern under inspection, and a detection optical system including a merging optical system which produces an optical image by merging the optical images, with a relative phase shift being imposed, and an opto-electric transducer means which receives the merged optical image and converts it into a signal, and pattern information is detected in the signal produced by the opto-electric transducer means in the detection optical system.

The inventive pattern detection apparatus comprises a detection optical means including a merging optical system which splits an illumination light of an illumination optical system, which illuminates a repetitive pattern with a coherent or partially coherent light, into multiple light beams, separates the optical images produced by the multiple illumination light beams, and produces an optical image by merging the optical images, with a relative phase shift being imposed, and an opto-electric transducer means which receives the merged optical image and converts it into a signal, and pattern information is detected in the signal produced by the opto-electric transducer means in the detection optical means.

The inventive method and apparatus are designed for repetitive patterns of one, two or three-dimensional arrays, or radial, angular or symmetric arrays by varying the magnification, angle or position.

The inventive method and apparatus are designed to merge optical images by use of the angular difference, positional difference or radiation difference of the light or the difference of polarization. The split, phase shift and merge optical system includes one or more in combination of a double-refraction element, a half mirror, multiple pin holes, multiple slits, a diffraction grating, multiple Fresnel zone plates, a plane mirror, a lens, concave/convex mirrors, a prism, and a hologram.

Objects of detection pertinent to the inventive method and apparatus include patterns of semiconductor wafers of LSI memories and TFTs (thin film transistors), conductor patterns of printed wiring boards and ceramic substrates, and patterns of masks and reticles used in the fabrication processes of these devices, as shown in FIG. 1. Although the following explanation takes an example of semiconductor wafer patterns, other patterns can be treated in the same manner.

FIG. 2A shows the surface of a semiconductor wafer on which dozens of chips, which are separated into independent devices, are arrayed. Each chip has a memory cell section 22 having a repetitive pattern, as shown by the magnified view in FIG. 2B for the portion A, and a peripheral circuit section 21 having a smaller degree of repetitiveness.

The principle of the present invention for detecting a defect of pattern will be explained with reference to FIGS. 1A to 1C. On the semiconductor wafer, all chips have exactly the same pattern, or all cells on a chip are formed in a repetitive pattern. If no defect exists in any of the patterns, there is virtually no difference among the patterns, or if a pattern includes a defect, that pattern will be different at the defective portion. Accordingly, by splitting the optical image of a pattern and merging the split images while applying a relative phase shift of $\pi$ for example, a small defect can be detected from the difference of images.

The principle of the invention will further be explained with reference to FIG. 4. The object pattern has a repetitive shape with a cell pitch of d in its cross section as shown in the figure, for example. When a plane wave is projected onto the chip surface, it produces a reflected light beam having wave surfaces of different amplitudes and phases depending on the shape of cross section, and it includes information on the pattern structure such as a defect. The depiction shown in the figure is based on the assumption of constant reflectivity and only variation of phase, for the sake of simple of explanation. The wave surface is depicted at the front for the place where the reflected light beam has a lead phase or at the rear for the place where it has a lag phase.

The reflected light beam is introduced to an interference optical system 3 (FIG. 3). In the interference optical system (split, phase shift and merge optical system) 3, the input light beam is split into two beams, the phase of one beam is shifted by $\pi$ for example relative to another beam so that the wave surface position $\alpha$ is shifted by the amount of cell pitch of d (this shift value will be termed "shear value", the shift direction will be termed "shear direction", and the relative shift operation will be termed "shearing" hereinafter), and the two light beams are merged. As a result of merging, the reflected light beams from cell portions of the same shape on the two adjacent cells cancel out with each other, and only light components of the reflected light beams coming from a defective portion are left. The sensor which detects the light components of defect detects the magnitude of light that is the square of the amplitude, In this manner, the sensor is only sensitive to defective portions, i.e., the sensor output is logically zero level for a normal portion and it has a significant level for a defective portion. Accordingly, a normal portion and a defective portion can be discriminated based on the presence or absence of the sensor output even if the pixel size of detection is relatively large. Consequently, a pattern difference extractor 5 can readily detect a defect from the sensor output, and the detection speed can be enhanced by setting the pixel size larger than the size of defects.

Although in the above explanation the plane wave is projected to the object for the simplicity of explanation, the light beam is not required to be the plane wave, provided that the light paths from light source to the sensor are equal.

BRIEF DESCRIPTION OF THE DRAWINGS

FIGS. 1A to 1C are diagrams used to explain an object pattern, of which:

FIG. 1A shows the image of a stored pattern;

FIG. 1B shows the image of a detected pattern;

FIG. 1C shows the image of a pattern difference produced from the stored pattern and detected pattern;

FIG. 2A is a diagram showing the pattern of a semiconductor wafer;

FIG. 2B is a diagram showing the magnified view for the portion A of FIG. 2A;

FIGS. 8A to 8C are diagrams used to explain the defect detection method based on this invention, of which:

FIG. 8A shows a detected pattern based on the ordinary ray;

FIG. 8B shows a shear detection pattern in the x direction; and

FIG. 8C shows a detected pattern in the y direction;

FIGS. 9A to 9C are diagrams showing exceptional patterns, of which:

FIG. 9A shows a corner pattern and an isolated pattern;

FIG. 9B shows the periphery of a repetitive pattern; and

FIG. 9C shows an oblique pattern;

FIG. 18 is a block diagram of the pattern detection apparatus based on the second embodiment of this invention;

FIGS. 19A and 19B are diagrams showing patterns used to adjust the shear direction, of which:

FIG. 19A shows a pattern of only x direction; and

FIG. 19B shows a pattern of only y direction;

DESCRIPTION OF THE PREFERRED EMBODIMENTS

Embodiments this invention will be explained with reference to the drawings.

Figure 3:
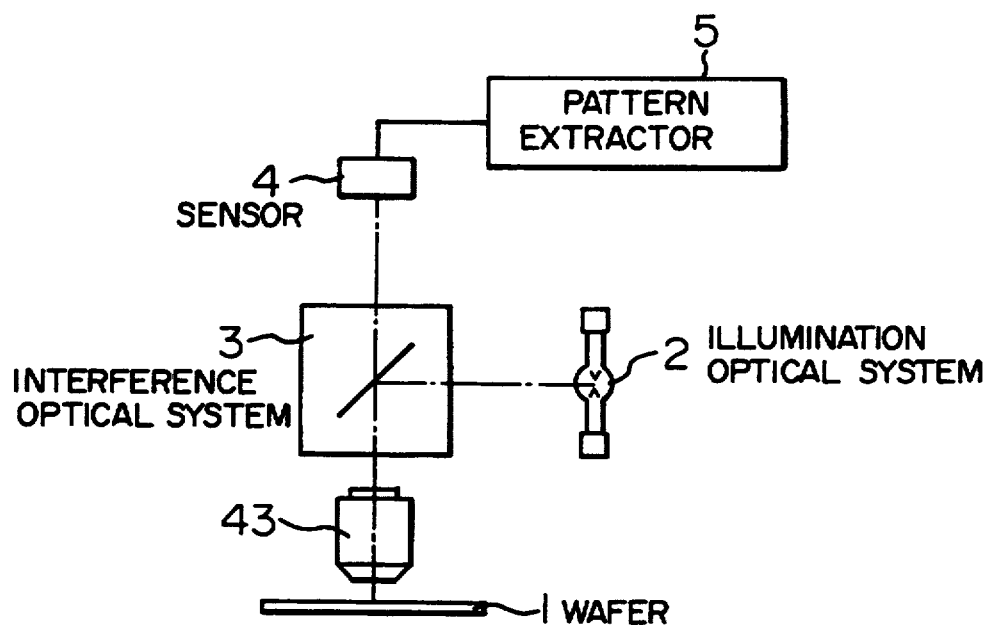
FIG. 3 is a block diagram showing the basic system configuration of this invention.
Figure 4:
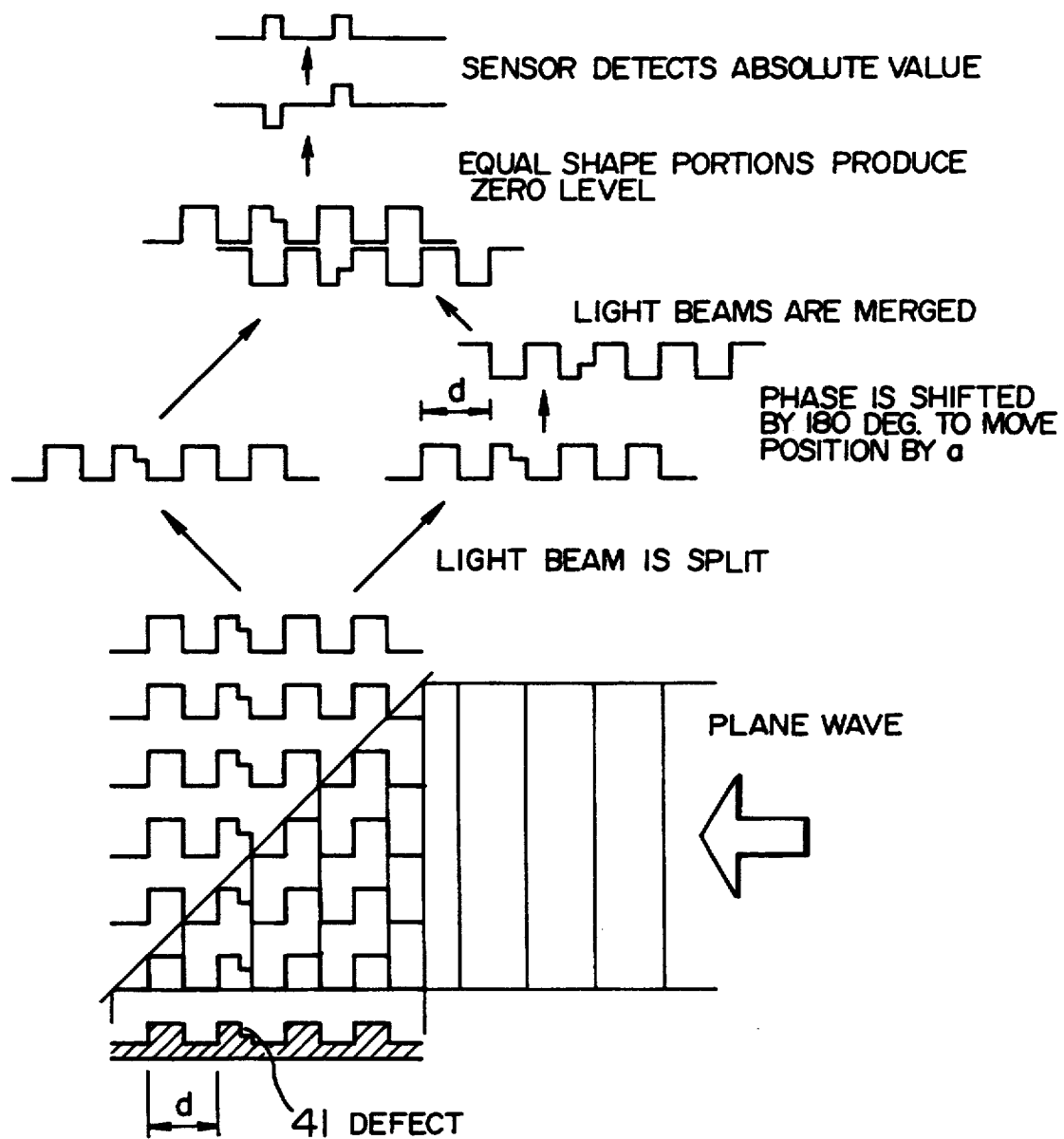
FIG. 4 is a diagram used to explain the principle of this invention.
Figure 6A:
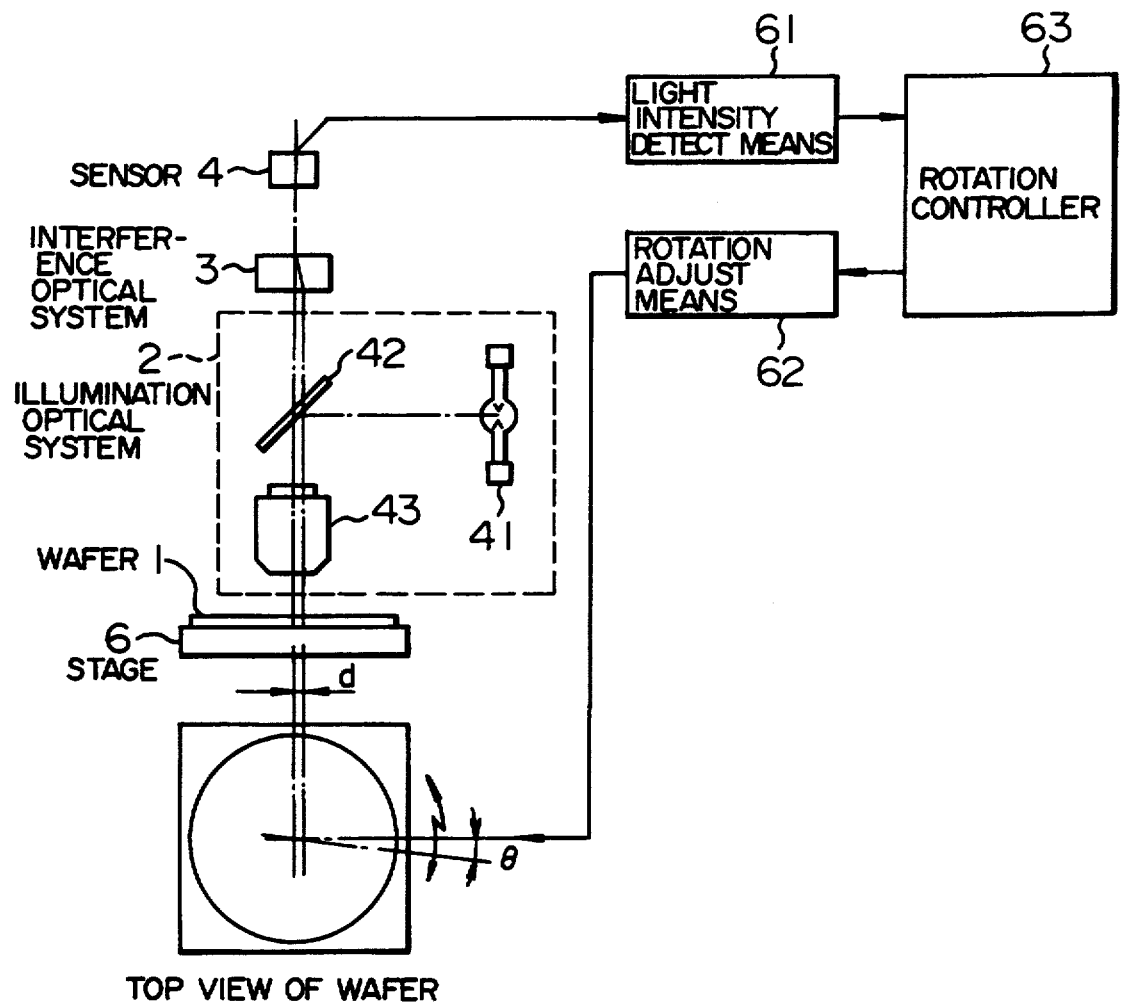
FIG. 6A is a block diagram of the arrangement for implementing the adjustment of the shear direction in the embodiment of FIG. 5A.

First, the basic system configuration of the invention will be explained with reference to FIG. 3. The inventive pattern detection apparatus comprises an illumination optical system 2 which illuminates with a coherent or partially coherent light beam an object of detection 1, as shown in FIG. 1, which is a pattern of a semiconductor wafer of an LSI memory or TFTs (thin film transistors), a conductor pattern of a printed wiring board or ceramic substrate, or a pattern of a mask or reticles used in the fabrication processes of the device, an interference optical system (split, phase shift and merge optical system) 3 which splits the illumination light beam or reflected detection light beam (optical image), and merges the optical images, with a relative phase shift being imposed, so that they interfere with each other thereby to detect the difference of patterns which are shared by the cell pitch, a sensor (opto-electric transducer means) 4 which detects the pattern difference, and a pattern difference extractor 5 which detects pattern information, such as a small defect, based on the difference of pattern. Illumination optical system 2 may be either outside of interference optical system 3, as depicted in FIG. 3, or within the interference optical systems, as depicted in FIG. 6A.

Figure 5A:
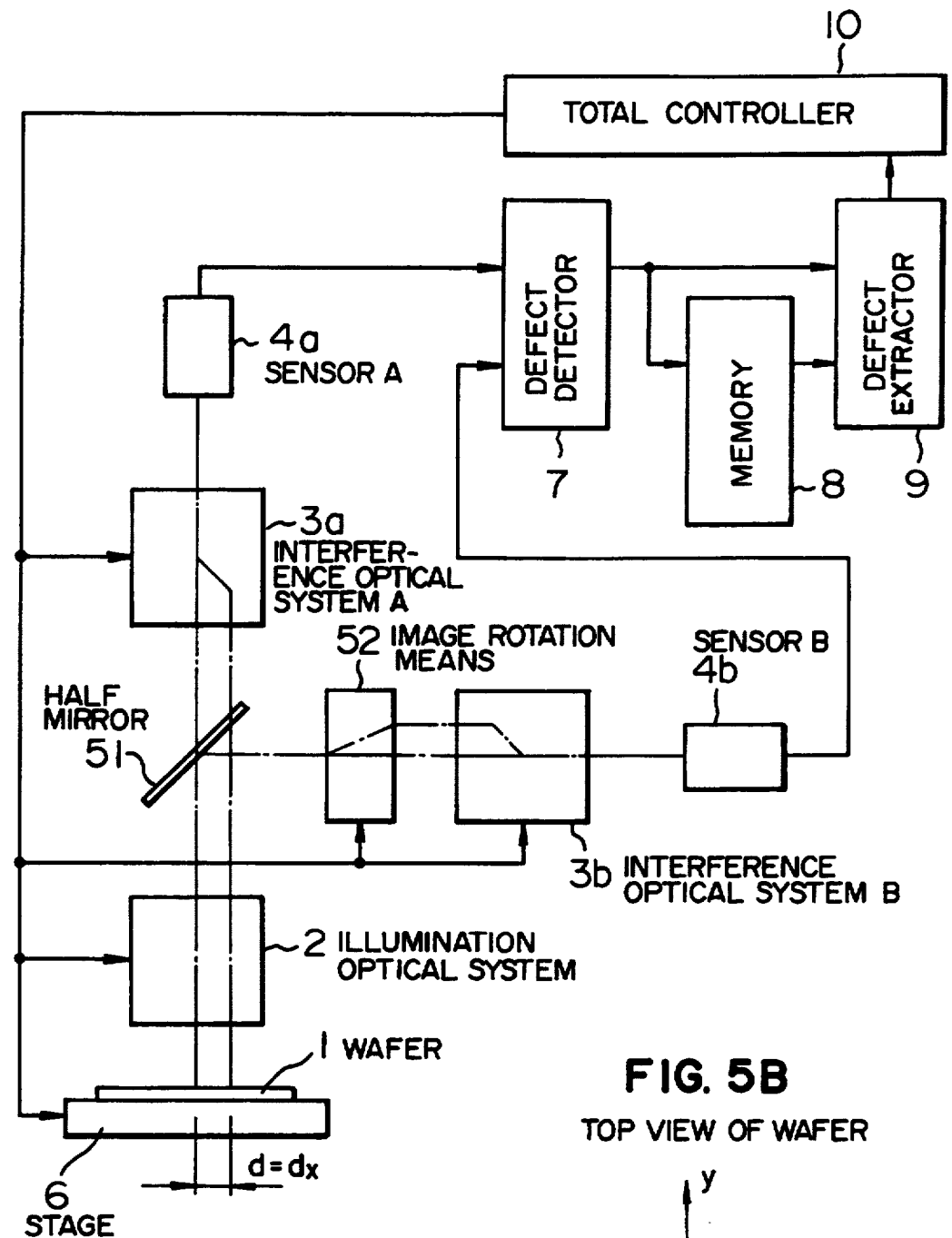
FIG. 5A is a block diagram of the pattern detection apparatus based on a first embodiment of this invention.

Next, the first embodiment of this invention will be explained with reference to FIGS. 5A and 5B. Although this embodiment deals with a pattern of an LSI wafer, it is of course applicable also to a pattern of TFTs and the like. FIG. 5A shows the overall arrangement of the apparatus for inspecting a repetitive pattern of an LSI wafer.

The inspection apparatus comprises a stage 6 for positioning a wafer (object of inspection) 1, an illumination optical system 2 which illuminates the wafer 1 and receives the reflected light, a half mirror 51 which separates the reflected light beam, an interference optical system (A) 3a which causes one separated light beam to interfere and extracts a pattern difference, a two-dimensional sensor (A) 4a such as a TV camera for detecting the pattern difference, an image rotation means 52 which rotates another light beam separated by the half mirror, an interference optical system (B) 3b which causes the rotated image to interfere and extracts a pattern difference, a two-dimensional sensor (B) 4b such as a TV camera for detecting the pattern difference provided by the interference optical system B, a defect detector 7 which detects a defective pattern based on the signals produced by the sensors A and B, a memory 8 which stores defective patterns as detected by the defect detector 7, a defect extractor 9 which compares the detected defective pattern with the defective pattern detected on the preceding chip as stored in the memory thereby to detecting a true defective pattern, and a total controller 10 which controls the whole apparatus including the stage, illumination optical system, image rotation means and interference optical system B.

All functional components of the apparatus designed to focus the images formed at point (a) 1052 and point (b) 1053, on intermediate image plane 1051, at point (c) 1054, on sensor 4. The polarizing shear values dx and dy in the x and y directions being set equal to the cell pitches in the x and y directions. This operation establishes an x-axis comparison position 12 and y-axis comparison position 13 with respect to a reference point 11. For this operation, coarse shear values dx and dy are set initially based on the design data, and the stage 6 is moved to a memory cell section 22 shown in FIG. 2.

Figure 6B:
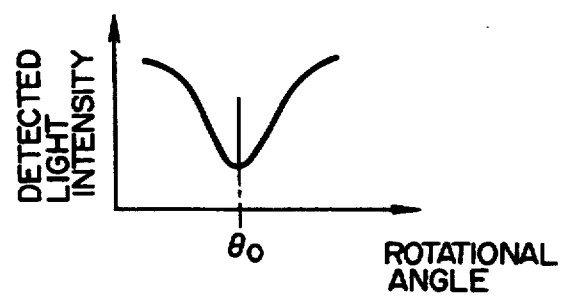
FIG. 6B is a graph showing the relation between the rotational angle and the detected light intensity.

The operation of aligning the x and y axes of the wafer coordinate system with the shear directions of the interference optical system 3 will be explained with reference to FIGS. 6A and 6B.

The rotation controller 63 in the total controller 10 operates on the rotation adjustment means 62 to drive the stage 6 so that the stage rotation angle $\theta$ is set with respect to the x and y axes of the wafer coordinate system at which the light intensity detection means 61 detects the minimum average light intensity of the sensor (A) 4a for the reflected optical image received by the illumination optical system 2 from the wafer 1. Next, the image rotation means 52 rotates the image, the light intensity detection means 61 detects the average light intensity of the sensor (B) 4b, and the rotation controller 63 in the total controller 10 sets the image rotation angle so that the detected light intensity is minimum.

Figure 7A:
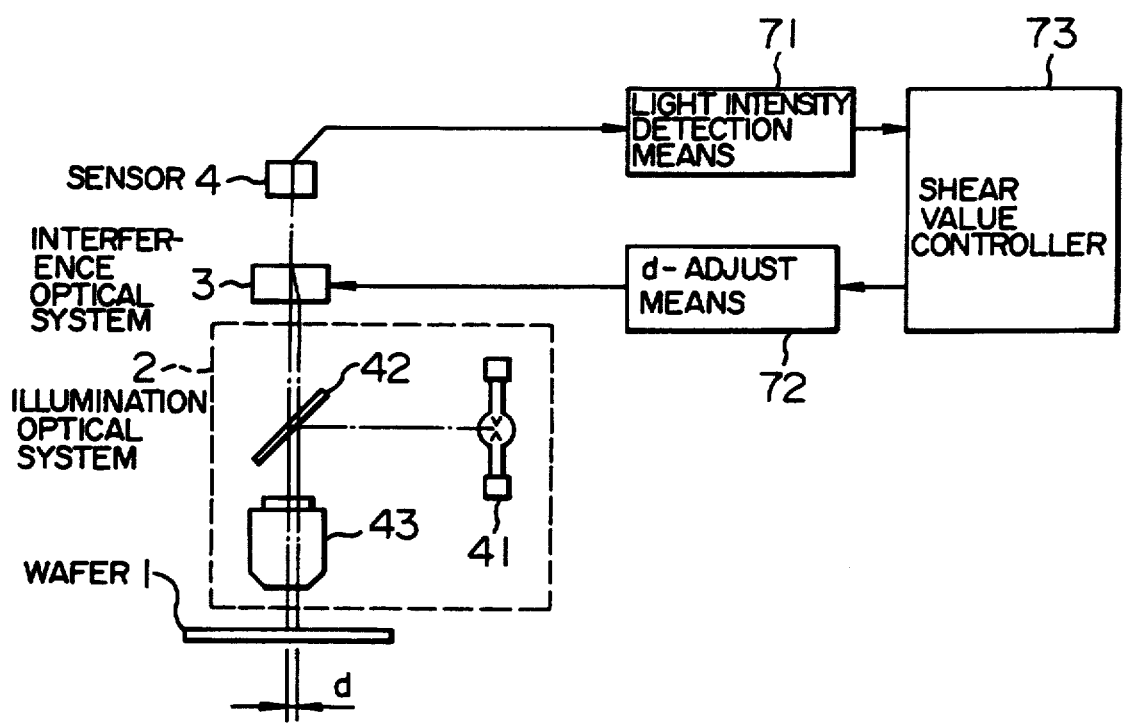
FIG. 7A is a block diagram of the arrangement for implementing the adjustment of the shear value in the embodiment of FIG. 5A.
Figure 7B:
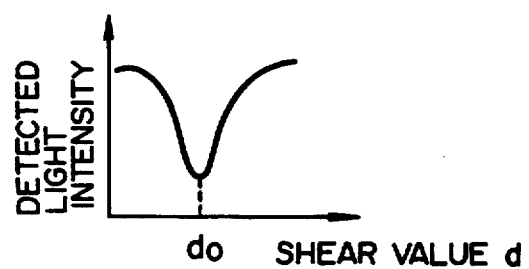
FIG. 7B is a graph showing the relation between the shear value and the detected light intensity.

Next, the operation of making the shear values dx and dy in the x and y directions equal to the cell pitches in the x and y directions will be explained on FIGS. 7A and 7B. The shear value controller 73 in the total controller 10 operates on the shear adjustment means 72 to adjust the interference optical system 3a so as to vary the shear value dx, with the average light intensity of the sensor A being detected with the light intensity detection means 71 (the detection means 61 may be used commonly), and the shear value dx is set at the minimum detected light intensity. Subsequently, the shear value controller 73 in the total controller 10 operates on the shear adjustment means 72 to adjust the interference optical system 3b so as to vary the shear value dy, with the average light intensity of the sensor B being detected, and the shear value dy is set at the minimum detected light intensity.

Figure 5B:
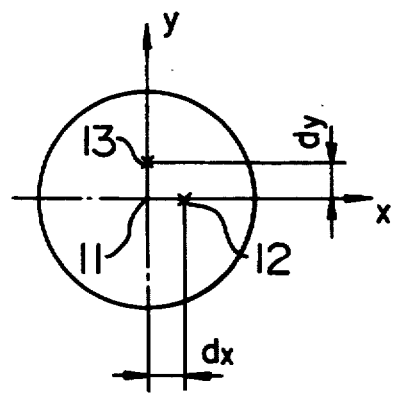
FIG. 5B is a diagram showing the top view of an object wafer.

Next, with the stage 6 being positioned as shown in FIG. 5B, the sensors A and B detect pattern differences and the defect detector 7 determines the smaller of the two pattern difference signals to be a defective pattern and stores it in the memory 8.

Another defective pattern is detected at the same position on the adjacent chip. The defect extractor 9 compares it with the stored defective pattern and extracts a portion with a non-zero value, where it is zero in the stored defective pattern, as a true defect. Following the judgement of defect, the detected defective pattern is stored in the memory 8, and the same operation takes place for the next chip. On completion of defect judgement on an object chip, the stage is positioned to another section of the wafer and the defect judgement is repeated.

The operation of defect judgement will be explained with reference to FIGS. 8A to 8C. FIG. 8A shows a detected pattern produced by the ordinary way, FIG. 8B shows a detected pattern produced by shearing interference in the x direction, and FIG. 8C shows a detected pattern produced by shearing in the y direction for interference. As a result of interference (split, phase shift and merge), two differences are detected for one defect, as shown in FIGS. 8B and 8C, because of the emergence of differences at a defective portion which is compared with a normal portion and also at the normal portion which is compared with a .defective portion. Since the sensor A and the sensor B compare patterns in directions of right angles, the defective portion is common in the two detected patterns, but the detected normal portions are in different positions in the detected patterns. Accordingly, through the selection of the smaller of the two detected patterns, the normal portions are eliminated and only the defective portion is left.

It should be noted that the result of the above process still includes normal portions detected as exceptional pattern portions at positions where the pattern is not repetitive in the x or y direction as shown in FIGS. 9A to 9C. Among these exceptional patterns, shown by FIG. 9A are a corner pattern and an isolated pattern, shown by 9B is the end of a pattern array, and shown by 9C is an oblique pattern. These exceptional patterns arise on all chips identically, while a true defect arises at random. Based on this fact, a detected defect at the position where no defect has been detected on the preceding chip is judged to be a true defect.

Figure 10:
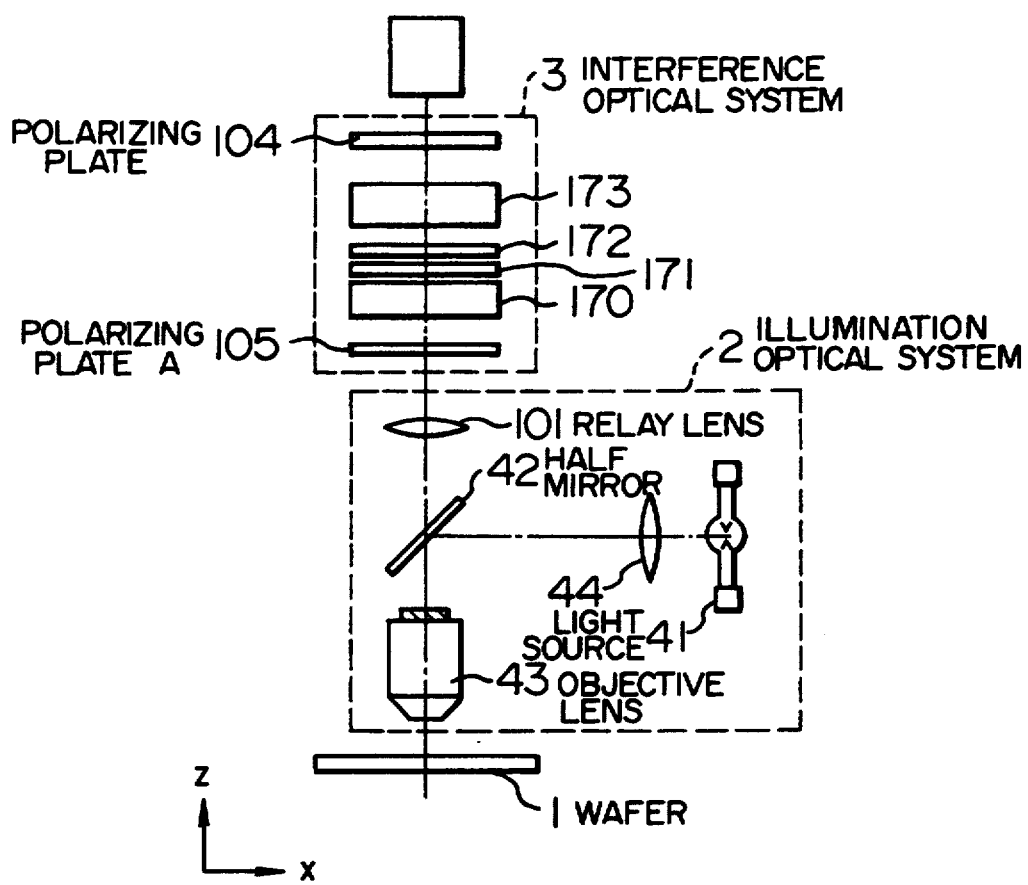
FIG. 10 is a block diagram showing the arrangement of the interference optical system based on an embodiment of this invention.

Next, the arrangement of the interference optical system (split, phase shift and merge optical system) based on this embodiment will be explained with reference to FIG. 10. In the illumination optical system 2, a light beam produced by the light source 41 is collimated by a lens 44, and it is projected onto the wafer 1 by way of the half mirror 42 and objective lens 43. Consequently, the wafer 1 is illuminated by a plane wave having the property of interference in multiple directions, i.e., partially coherent illumination. Since a partially coherent light beam has no interference between light components in different directions or of different wavelengths, a pattern difference can be extracted if the interferences (split, phase shift and merge) by dealing with only a plane wave with one wavelength and in one direction are all same or almost same.

The reflected light beam goes through the objective lens 43 and a relay lens 101 and enters the interference optical system 3. The interference optical system 3 comprises a polarizing plate (A) 105, a parallel double-refraction element plate 170, a halfwave plate 171, another halfwave plate 172, another parallel double-refraction element plate 173, and another polarizing plate 104.

Figure 11:
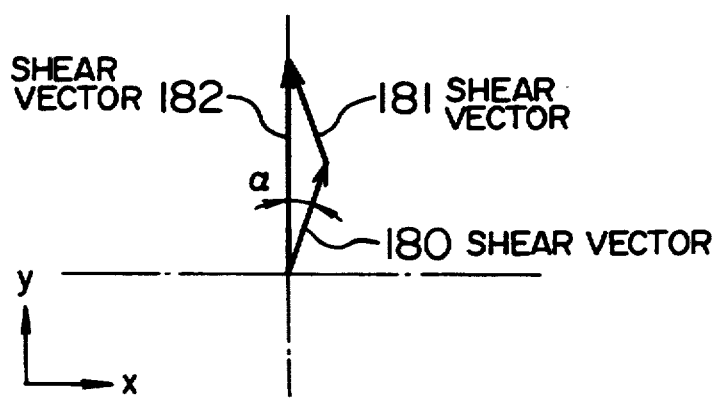
FIG. 11 is a diagram showing the shear vector in the interference optical system.

The operation of the interference optical system 3 will be explained with reference to FIG. 11. FIG. 11 is a top view of the interference optical system 3, showing in a vectorial manner the parallel shift (called shear) of light beams which is incident to the interference optical system at a distance of d between both light beams on the object (wafer 1). When two light beams spaced out by a distance of d enter the interference optical system 3, the parallel double-refraction element plate 170 shears (parallel shift of one beam relative to another beam) light beams for the amount of a shear vector 180 which inclines by an angle of α with respect to the target shear direction, and another parallel double-refraction element plate 173 shears the light beam for the amount of a shear vector 181, resulting in a total shear indicated by a shear vector 182, and if the shear vector 182 is equal in distance and direction to the distance d on the object (wafer 1), the two light beams become a single light beam and they interfere (merge) with each other.

Figure 12:
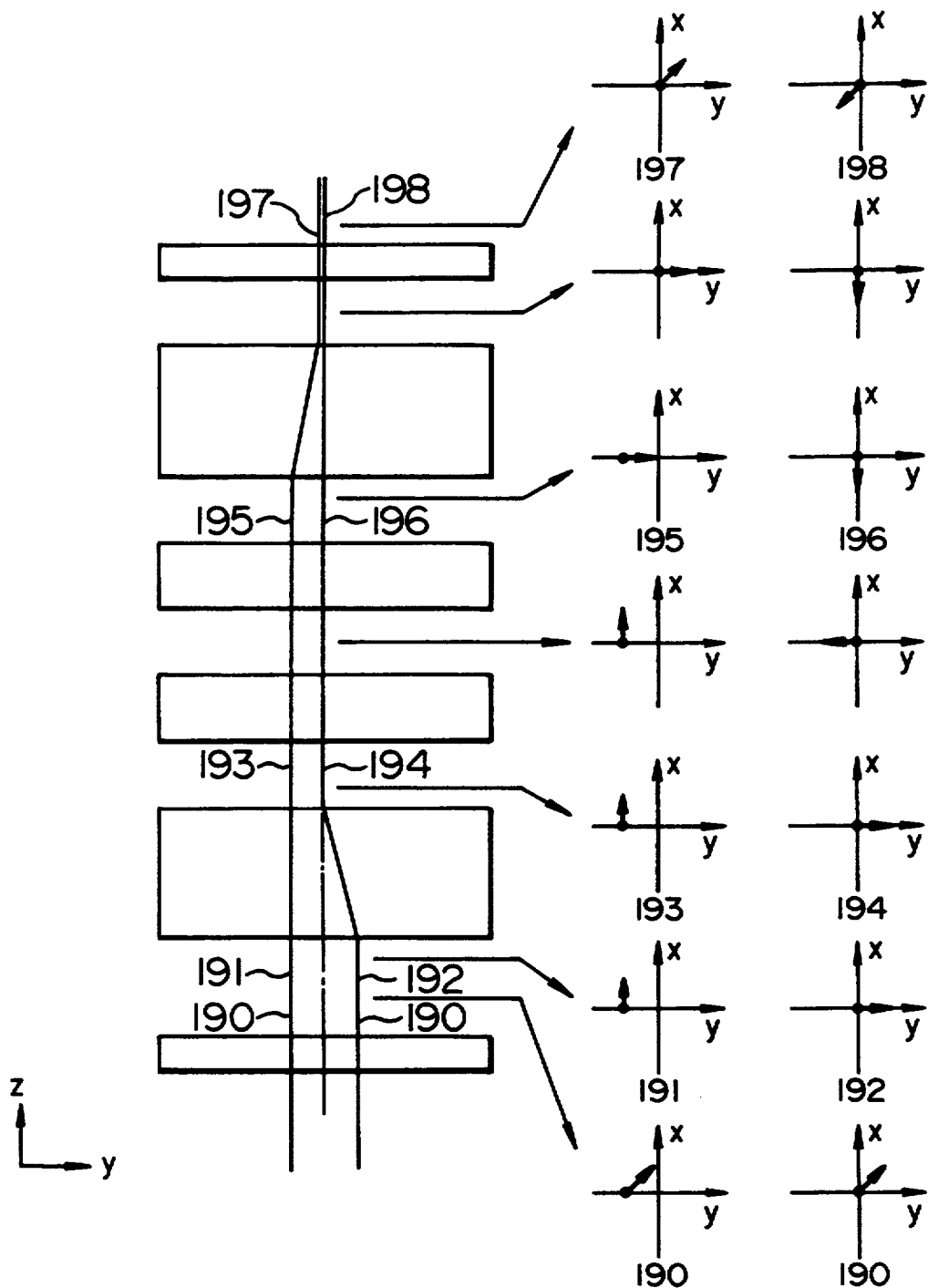
FIG. 12 is a diagram used to explain the principle of interference in the interference optical system.

The above-mentioned operation will be explained in more detail with reference to FIG. 12, which explains the major functional components in the interference optical system (split, phase shift and merge optical system). The figure depicts the light paths in the y-z plane and also shows in vectorial manner the light beam positions and polarizing directions at the principal sections, The left and right columns of the vectorial diagram are for the left and right light beams. For the simplicity of explanation, the case of the shear vectors 180, 181 and 182 having the same direction will first be explained. The polarizing plate 105 converts the two input light beams into linearly polarized light beams 190 which are 45° rotated to the optical axis of the parallel double-refraction element plate 170. The linearly polarized light beams 190 can be considered to be a vector sum of linearly polarized light beams in two directions, i.e., the sum of components in the ordinary ray direction 191 and extraordinary ray direction 192 of the parallel double-refraction element plate 170. Attention is paid to a light beam 193 of the ordinary ray direction for one light beam and a light beam 194 of the extraordinary ray direction for another light beam. The ordinary ray component 193 goes straight through the parallel double-refraction element plate 170, while the extraordinary ray component 194 goes by shearing in the x direction by the amount of the shear vector 180.

These light beams are incident to the halfwave plate 171 having the optical axis set to the direction of shear vector 182, and consequently the extraordinary ray component 194 leads the ordinary ray component 193 by a phase of #. The light beams are further incident to the halfwave plate 172 having the optical axis set to the bisected angle of the ordinary and extraordinary ray components 193 and 194 for the reversion of polarizing direction so that the ordinary ray component 193 is converted to an extraordinary ray component 195 and the extraordinary ray component 194 is converted to an ordinary ray component 196. The converted light beams 195 and 196 are incident to the parallel double-refraction element plate 173 having the optical axis rotated by 180° with respect to the shear vector 181 for providing the shear addition (merging) by the amount of the shear vector 181, resulting in output light beams having a shear of the shear vector 182. These light beams are incident to the polarizing plate 104 which does not transmit the polarized ray in the direction of the bisected angle of the extraordinary ray component 194 and ordinary ray component 196 so that the two light beams-interfere (merge), with their polarized components being made equal, resulting in output light beams 197 and 198 for which the light detection output is zero when the two light beams have the same amplitude.

In the case of the shear vectors 180, 181 and 182 having different directions, the halfwave plate 171 is used to convert the shear vector 180 into the shear vector 181, and the same performance is accomplished. In regard to the matter of a partially coherent light beam, if the difference of light path lengths is less than one tenth of the wavelength and the difference of shear values of the parallel double-refraction element plates 170 and 171 is small, the above-mentioned condition of pattern difference extraction is satisfied. This operation can be realized by use of devices having smaller wavelength dependency or use of wavelengths in a narrow band. Much detailed explanation is omitted since this topic is not the essence of the present invention.

This embodiment provides the following effectiveness.

(1) The result of comparison of two cells in a chip pattern of a wafer is compared with the comparison result of another chip, and a defect is detected through the comparison of the two cells instead of using design data, although portions of a chip where two cell cannot be compared cannot be inspected.

(2) In the interference optical system (split, phase shift and merge optical system) 3, two light beams which are subjected to interference (split, phase shift and merge) are conducted on the same light path, and therefore the operation is stable.

(3) The shear value and shear direction are corrected at the time of initialization, and therefore the apparatus is readily responsive to objects of different cell pitches.

(4) Through the selection of the smaller of the results of two-cell comparison in the x and y directions, a true defect can be detected at sections where two cells can be compared.

(5) The interference optical system (split, phase shift and merge optical system) 3 includes the polarizing plates 105 and 104, which enables the conversion of a reflected light beam into a linearly polarized light beam even from an elliptically polarized light beam, and therefore the operation is not influenced by the difference of the P and S polarization caused by the elliptically polarized light.

In consequence, the automatic inspection of patterns is possible for sections of a wafer where two cells can be compared.

Next, the first variant embodiment of the interference optical system (split, phase shift and merge optical system) 3 will be explained. The two pieces of halfwave plates 171 and 172 in the foregoing embodiment are formed as a single piece. This modification results in a simpler structure of the apparatus, although the setting of the rotational angle for varying the shear value will become intricate.

Next, the second variant embodiment of the interference optical system (split, phase shift and merge optical system) 3 will be explained. The two halfwave plates 171 and 172 are formed of optical rotary elements such as liquid crystal elements or Kerr elements, and the polarization of the two parallel double-refraction element plates 170 and 173 is adjusted by varying the application voltage or the like. This modification reduces the number of moving components and enhances the reliability of the apparatus.

Next, the third variant embodiment will be explained. The image rotating means 52 is designed to rotate the two interference optical systems 3a and 3b. This modification enables the adjustment of the shear direction without the need of rotating the object (wafer) 1.

Figure 13:
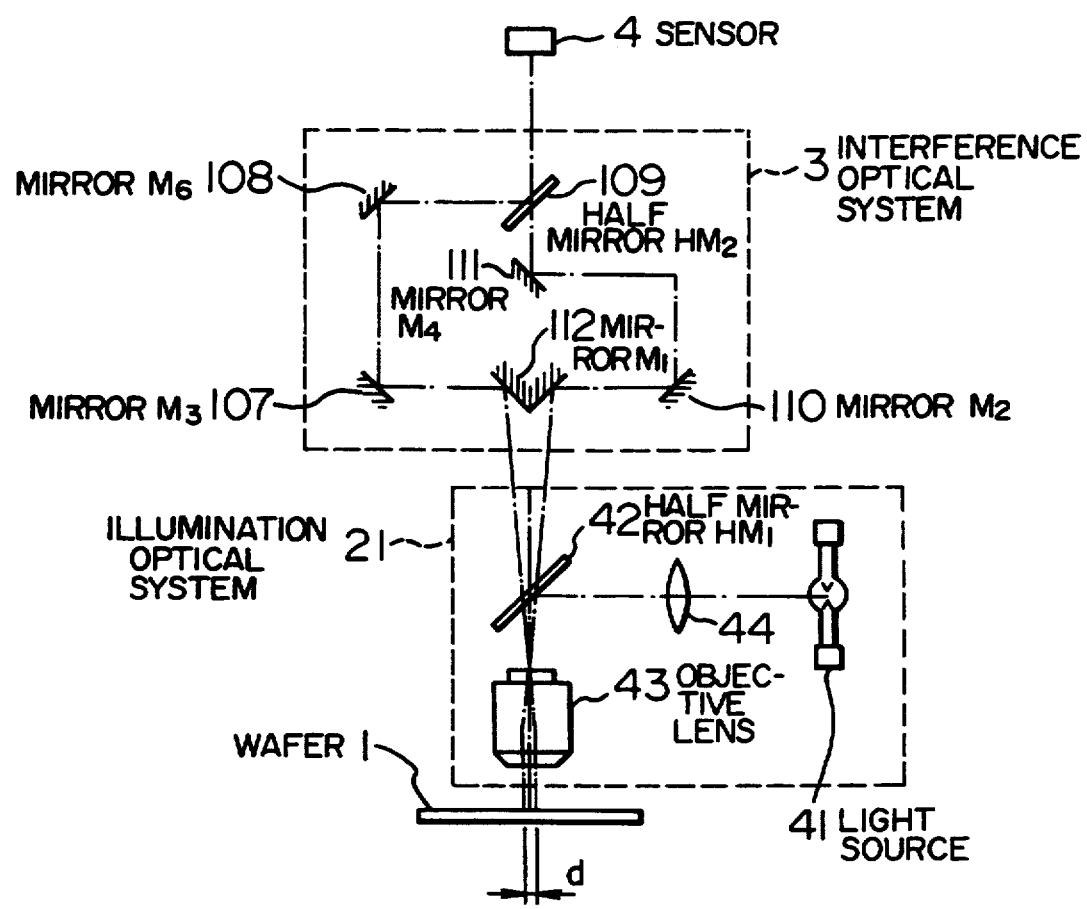
FIG. 13 is a block diagram of a first variant embodiment of the interference optical system shown in FIG. 10.

Next, the fourth variant embodiment will be explained. FIG. 13 shows the arrangement of the interference optical system (split, phase shift and merge optical system) 3. The optical system comprises a mirror 112 which splits the light beam on the intermediate image plane of the objective lens 43, and a set of mirrors 107, 108, 110 and 111 and a half mirror 109 which unifies the split light beams. The light beams are conducted on different light paths, and then merged to provide a shear value of d. The shear value is set by moving one or more mirrors.

Figure 14:
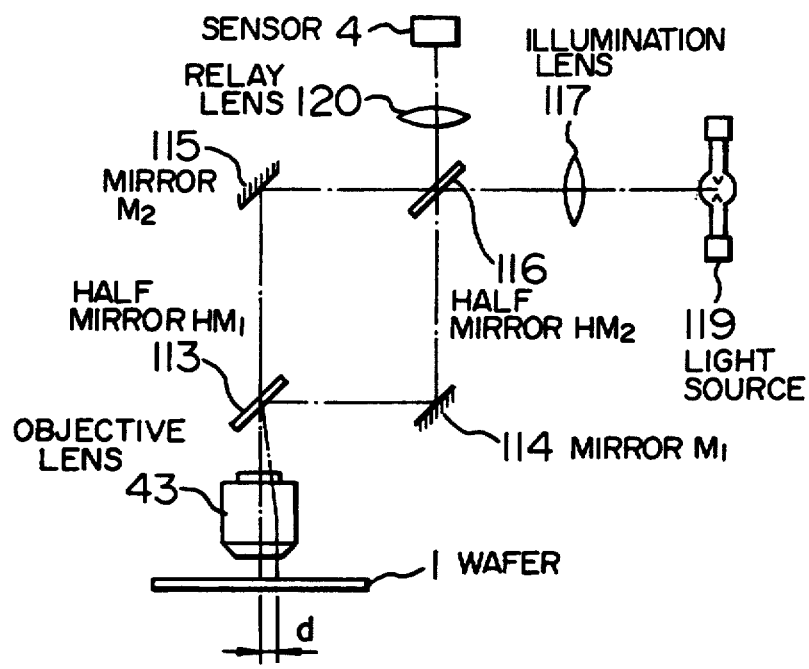
FIG. 14 is a block diagram of a second variant embodiment of the interference optical system shown in FIG. 10.
Figure 15:
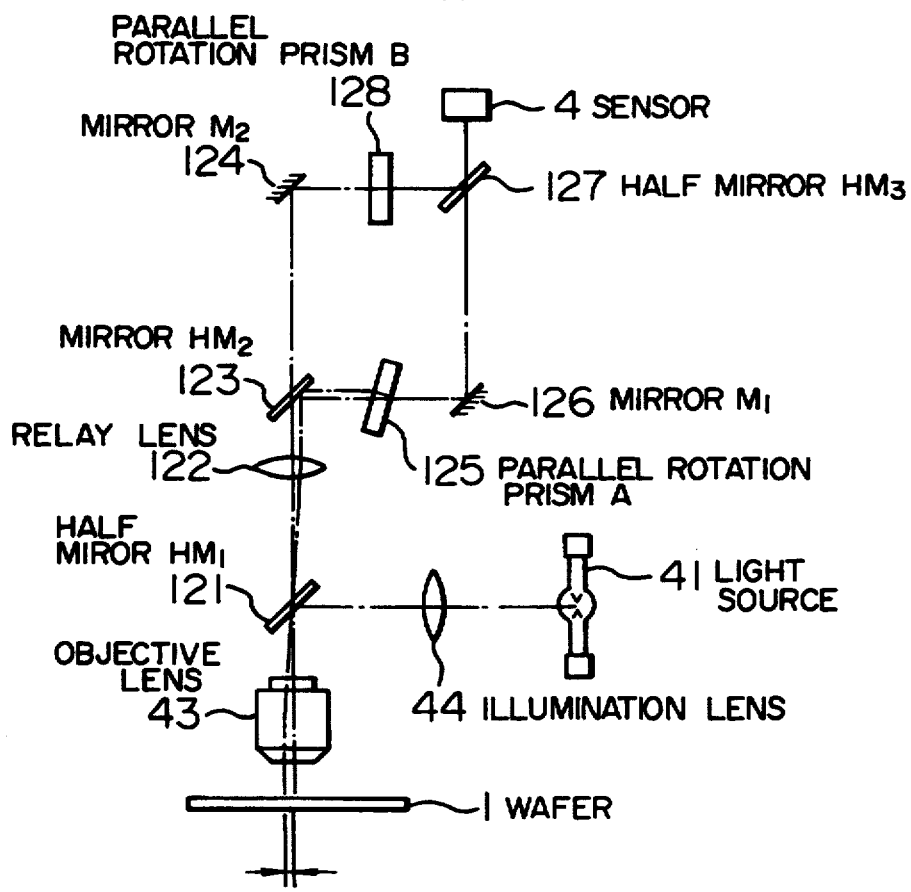
FIG. 15 is a block diagram of a third variant embodiment of the interference optical system shown in FIG. 10.

Further variations of this embodiment are shown in FIG. 14 and FIG. 15, in which the light beam is split by a half mirror 113 or 123, and the beams are unified by a pair of mirrors 114 and 115 or a pair of mirrors 124 and 126, and a half mirror 116 or 127.

In the arrangement of FIG. 13, the mirrors 113, 114, 115 and 116 serve also for the illumination optical system. Shown by 119 in FIG. 14 is a light source and 117 is an illumination lens. The arrangement of FIG. 15 includes a relay lens 122, and it further differs from FIG. 14 in the adjustment of shear value by means of parallel rotary prisms 125 and 128, instead of the movement of the mirrors. Any of these variant embodiments does not use the polarization, and therefore it does not need to consider the property of polarization of the object.

Figure 16A:
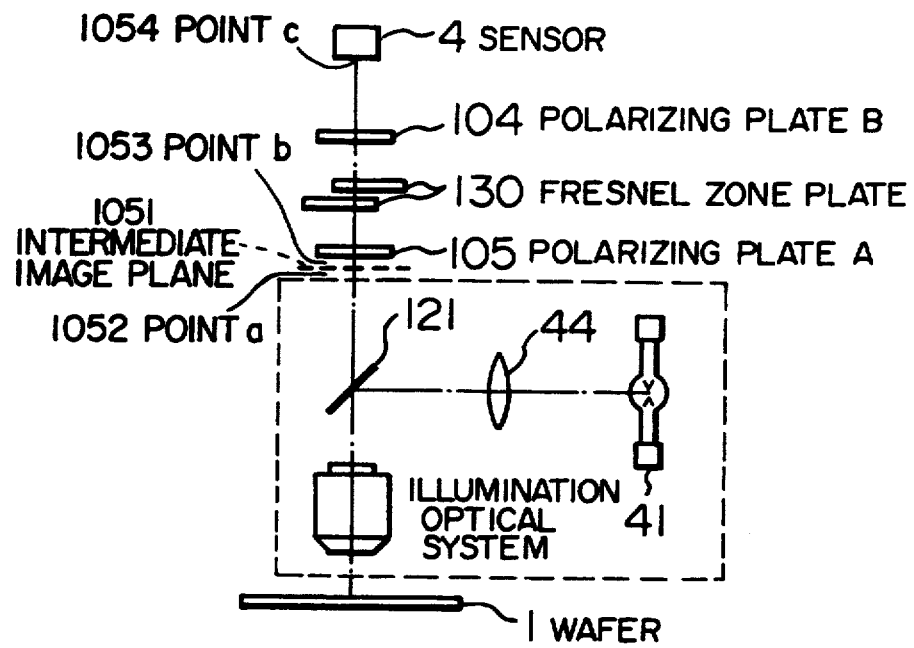
FIG. 16A is a block diagram of a fourth variant embodiment of the interference optical system shown in FIG. 10.
Figure 16B:
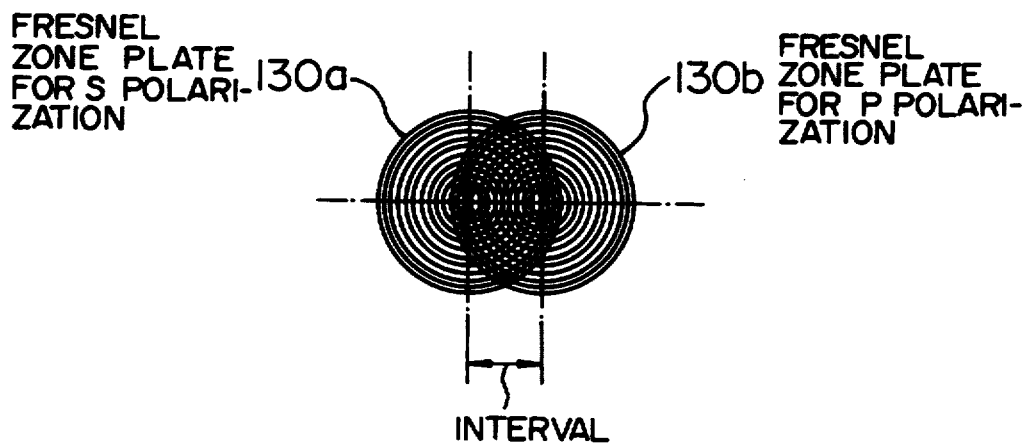
FIG. 16B is a diagram showing the structure of the Fresnel zone plate.

Next, the fifth variant embodiment will be explained. FIG. 16A shows the arrangement of the interference optical system (split, phase shift and merge optical system) 3. The optical system is designed to split a light beam and then merge the two beams on the intermediate image plane between the polarizing plate (A) 105 and objective lens by means of a pair of Fresnel zone plates 130 capable of varying the distance of two beams shown in FIG. 16B and a polarizing plate (B) 104. The polarizing plate (A) 105 is placed at an angle of 45° with respect to the shift direction of the Fresnel zone plates thereby to equalize the P and S polarization components. The two Fresnel zone plates 130a and 130b are formed of polarizing plates, and are designed to act on only the P or S polarization component thereby to focus only the P or S polarization component at point c among the light at point a and point b of the intermediate image plane. The polarizing plate (B) 104 is placed at an angle of 45° with respect to the shift direction of the Fresnel zone plates, and it functions to rectify the polarization directions of the light so as to induce the interference. The shear value d can be adjusted by varying the distance of the Fresnel zone plates 130a and 130b.

Figure 17:
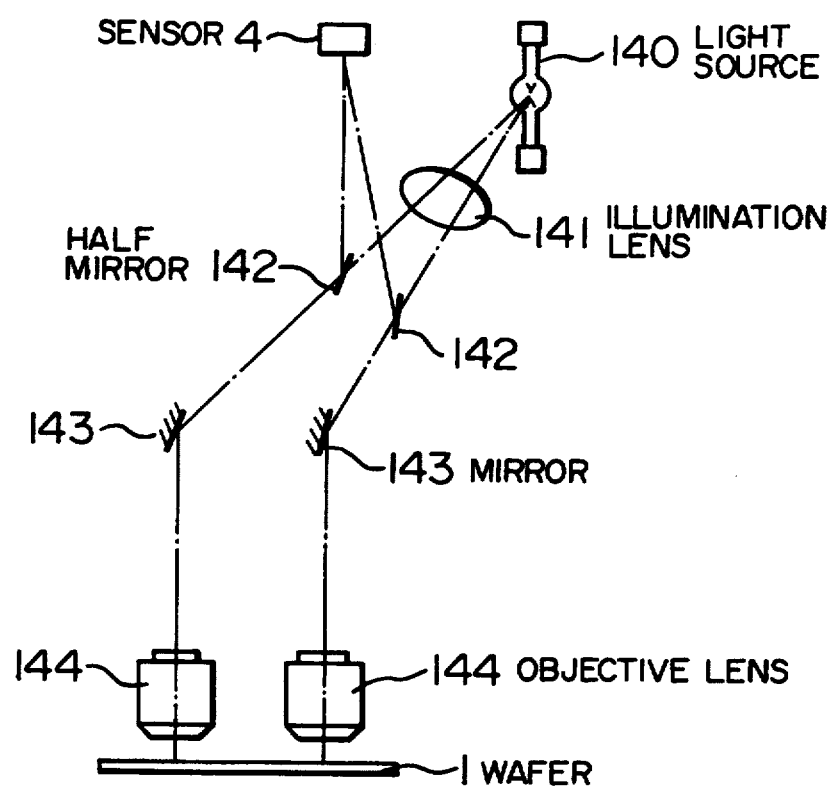
FIG. 17 is a block diagram of a fifth variant embodiment of the interference optical system shown in FIG. 10.

Next, the sixth variant embodiment will be explained. FIG. 17 shows the arrangement of the interference optical system (split, phase shift and merge optical system) 3. Two objective lenses 144 are used so that two optical images conducted by way of mirrors 143 and half mirrors 142 interfere (merge) on the sensor 4, and the images can be compared. The shear value is set by varying the distance of the objective lenses 144. This modified embodiment facilitates the comparison of distant portions, enabling the comparison of two chip patterns on a wafer or circuit patterns on two printed circuit boards.

Next, the seventh variant embodiment will be explained. A zoom relay lens is placed at the front of the interference optical system (split, phase shift and merge optical system) 3, and the shear value is made variable by varying the magnification factor of the lens. This modified embodiment simplifies the interference optical system 3.

Next, the eighth variant embodiment will be explained. A laser source is used for the illumination light source. This modified embodiment can elongate the distance of interference, allowing different light path lengths in the interference optical system, and it facilitates the adjustment.

Next, the ninth variant embodiment will be explained. As the pattern sensor 4 for the detection of pattern difference, a linear image sensor or point-type sensor can be used. This modified embodiment enables the stage 6 to move continuously, substituting for the step-and-repeat movement, allowing high-speed inspection for a wide area.

Next, the tenth variant embodiment will be explained. An optical image of a pattern is detected in addition to the pattern difference detected by the interference optical system 3 so that exceptional patterns as shown in FIG. 9 are inspected based on the image signal of the pattern. This modified embodiment enables the inspection of the whole area of the object.

Next, the eleventh variant embodiment will be explained. For an exceptional pattern as shown in FIG. 9, the degree of pattern difference is compared between two chips and the difference is determined to be a defect only if the difference is great significantly. This modified embodiment enables the inspection of the whole area of the object.

Next, the pattern detection apparatus based on the second embodiment of this invention will be explained with reference to FIG. 18. FIG. 18 shows the overall arrangement of a comparison microscope which compares two cells of a wafer pattern. The comparison microscope consists of an illumination optical system 2, a sensor (C) 151 which detects the light coming from the illumination optical system, a pair of interference optical systems (A, B) 3a and 3b for the x and y directions which operate under control of shear direction/value controllers (A, B) 152 and 153 in accordance with the signals provided by sensors (A, B) 4a and 4b, respectively, a pair of sensors (A, B) 4a and 4b which detect pattern differences produced by the interference optical systems 3a and 3b, a minimum value detection circuit 154 which extracts a defective pattern represented by the smaller of the output signals of the sensors 4a and 4b, a monitor unit 156 which receives through a switch/merge circuit 155 the pattern differences detected by the sensors 4a and 4b, a pattern image detected by a sensor (C) 151 and the output of the minimum value detection circuit 154, and a shear direction/value control switch 157 which controls the shear direction and shear value of the interference optical system 3.

Figure 19A:
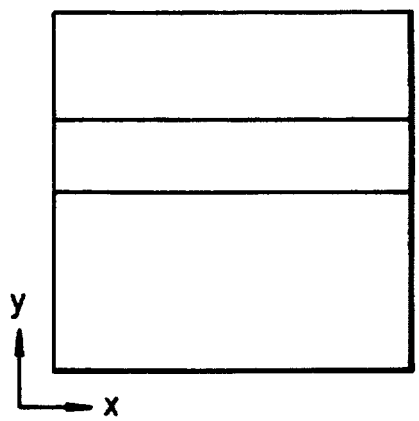

Next, the operation of the comparison microscope will be explained for the case of comparing two cells of a wafer pattern. The stage 6 is positioned by the manual operation of the operator who views the image on the monitor unit 156 which is set to receive the output of the sensor (C) 151 or by the program stored in the total controller 10, so that a wafer 1 mounted on it is sighted at a portion including only lines in the x direction as shown in FIG. 19A. The operator presses the switch 157, and the shear direction/value controller (A) 152 implements the adjustment of the shear direction of the interference optical system (A) 3a for the x direction in accordance with the signal from the sensor (A) 4a by following the procedure explained in the first embodiment.

Figure 19B:
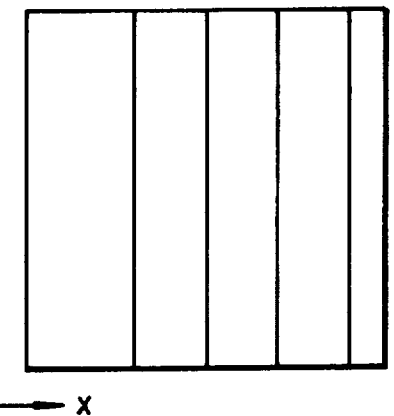

Next, the wafer pattern is positioned at a portion including only lines in the y direction as shown in FIG. 19B by the manual operation of the operator who views the image on the monitor unit 156 which is set to receive the output of the sensor (C) 151 or by the program stored in the total controller 10. The operator presses the switch 157, and the shear direction/value controller (B) 153 implements the adjustment of the shear direction of the interference optical system (B) 3b for the y direction in accordance with the signal from the sensor (B) 4b by following the procedure explained in the first embodiment.

Next, the stage 6 is positioned at a predetermined position so as to bring the cell section into the view field by the manual operation of the operator who views the image on the monitor unit 156 or by the program stored in the total controller 10. The operator presses the switch 157, and the shear values in the x and y directions are adjusted in the same manner as explained in the first embodiment.

The initialization of the apparatus for the pattern observation is now completed, and it is ready to display a defective pattern based on the pattern differences in the x and y directions detected in the image signals of the sensors (A, B) 4a and 4b and the signal produced by the minimum value detection circuit 154 and display a pattern portion based on the signal provided by the sensor (C) 151, through the switching of the switch-/merge circuit 155. It is also possible to merge these images on the monitor screen. For example, a defective pattern detected by the minimum value detection circuit 154 is displayed in red on a monochrome tone image of a wafer pattern detected by the control circuit (C) 151.

This embodiment provides the following effectiveness which is similar to that of the first embodiment.
(1) The shear value and other parameter are corrected at the time of initialization, and therefore the apparatus can readily treat objects of different cell pitches. The correction can be done without the need of preliminary information of the cell pitch, and therefore the scanning operation is made easy.
(2) Through the selection of the smaller of the results of two-cell comparison in the x and y directions, a true defect can be detected at sections where two cells can be compared.
(3) The interference optical system includes the polarizing plates, which enables the conversion of a reflected light beam into a linearly polarized light beam even from an elliptically polarized light beam, and therefore the operation is not influenced by the difference of the P and S polarization caused by the elliptically polarized light.
(4) The electric circuit which performs the two-cell comparison can be made very compact.

In consequence, only defects can be observed easily for sections of a wafer where two cells can be compared.

Figure 20:
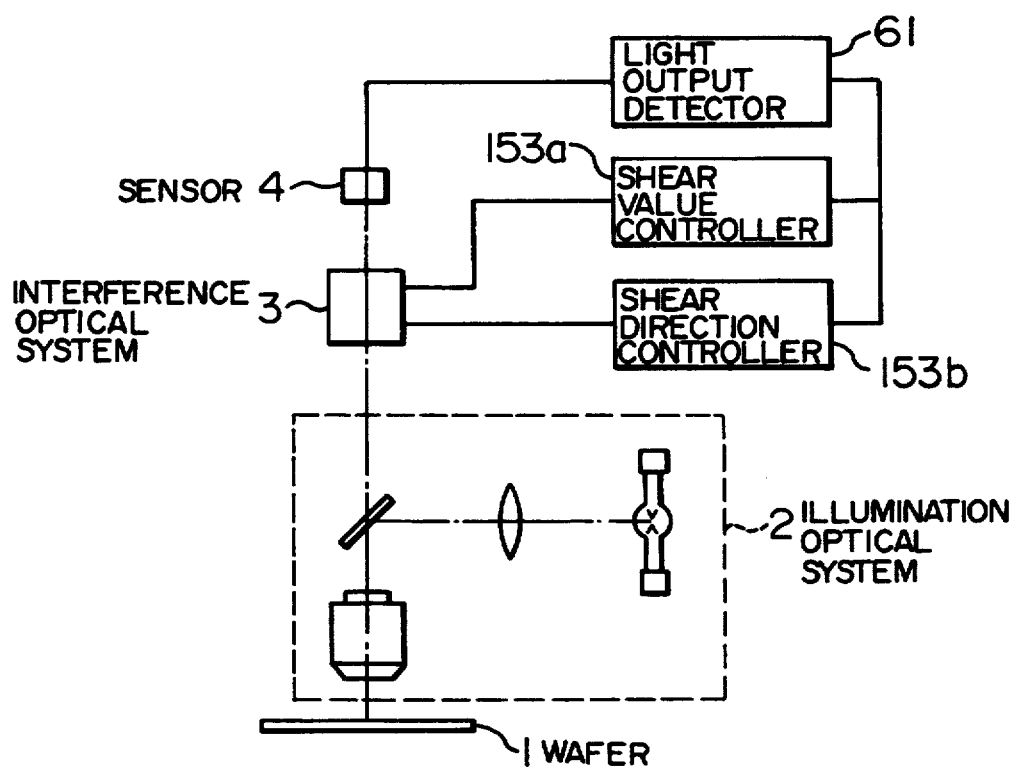
FIG. 20 is a block diagram of the pattern detection apparatus based on the third embodiment of this invention.

Next, the pattern detection apparatus based on the third embodiment of this invention will be explained with reference to FIG. 20. The figure shows the overall arrangement of the pitch measuring apparatus which measures the cell pitch and the like of a wafer pattern. The pitch measuring apparatus consists of an illumination optical system 2, an interference optical system 3 which adjusts the shear direction and shear value, a pattern difference sensor 4 which detects the pattern difference produced by the interference optical system, a light intensity detector 61 which measures the average light intensity based on the signal provided by the pattern difference sensor 4, a shear direction controller 153b which controls the shear direction of the interference optical system so that the average light intensity measured by the light intensity detector is minimum, a shear value controller 153a which controls the shear value of the interference optical system so that the average light intensity measured by the light intensity detector is minimum and displays the resulting shear value on a monitor unit incorporate in it, and a switch (not shown) which switches the control between the shear direction and shear value of the interference optical system.

Next, the operation of the pitch measuring apparatus will be explained for the case of measuring the cell pitch of a wafer pattern. The stage 6 is positioned so that a wafer 1 mounted on it is sighted at a portion including only lines in the x direction as shown in FIG. 19A, and the switch (not shown) is set to select the control of shear direction. Then, the shear direction controller 153b adjusts the shear direction of the interference optical system 3 for the x direction in accordance with the output signal of the light intensity detector 61. Next, the stage is positioned so that the wafer is sighted at a cell section, and the switch is operated to select the control of shear value. Then, the shear value controller 153a controls the shear value of the interference optical system 3 by varying the shear value in accordance with the output signal of the light intensity detector 61 so that the average light intensity is minimum. The displayed shear value is the result of measurement. More accurate measurement is possible by implementing the prior calibration of the shear value based on a sample with a known pattern pitch. As an effectiveness of this embodiment, it is capable of measuring the pattern pitch along the shear direction which is obtained in advance.

Figure 21:
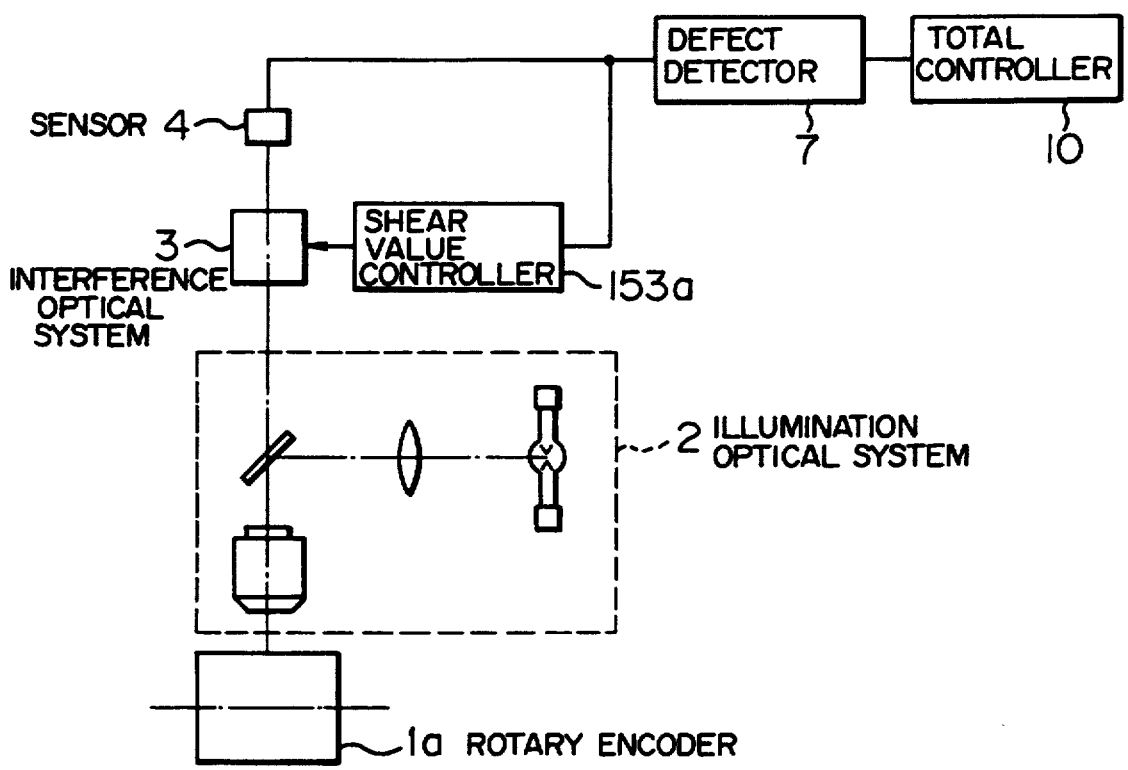
FIG. 21 is a block diagram of the pattern detection apparatus based on the fourth embodiment of this invention.
Figure 22:
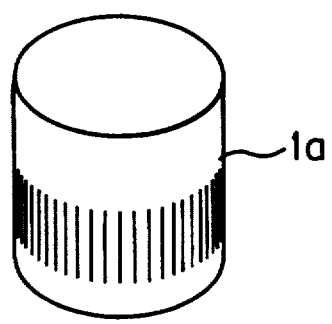
FIG. 22 is a diagram showing the pattern of a rotary encoder which is the object of detection of the fourth embodiment shown in FIG. 21.

Next, the pattern detection apparatus based on the fourth embodiment of this invention will be explained with reference to FIG. 21. The figure shows the overall arrangement of a pattern inspection apparatus which tests such a device as a rotary encoder. The rotary encoder 1a is a cylindrical body, with linear patterns being formed at a constant interval on the exterior surface as shown in FIG. 22. The inspection apparatus consists of a stage (not shown) for positioning the rotary encoder 1a, an illumination optical system 2 which illuminates the rotary encoder and detects the reflected light, an interference optical system 3 which causes the reflected light to interfere and extracts a pattern difference, a sensor 4 which detects the pattern difference, a defect detector 7 which detects a defect based on the signal provided by the sensor 4, a total controller 10 which controls the whole apparatus, and a shear value control means 153a which adjusts the shear value of the interference optical system 3 in accordance with the output of the sensor 4.

These functional components operate to detect a pattern defect as follows. Initially, as an initializing operation, the shear value controller 153a responds to the command of the total controller 10 to set the shear value d of the interference optical system 3 equal to the pattern pitch of the encoder in accordance with the output signal of the sensor 4. Next, the rotary encoder 1a placed on the stage (not shown) is rotated, and a pattern difference of the encoder is detected. Consequently, the defect detector 7 detects only a pattern difference which does not have repetitiveness. The total controller 10 registers coordinates of two points which were compared at the occurrence of a pattern difference, and it extracts a true defect by eliminating coordinates which were registered only as a single point.

A difference of dealing with a one-dimensional pattern from dealing with a two-dimensional pattern is that the pattern can be inspected by merely setting the shear value equal to the pattern pitch even if the shear direction deviates from the direction of repetitive pattern. As an effectiveness of this embodiment, defective patterns of such a device as a rotary encoder can be inspected with the apparatus of simple arrangement.

Next, the first variant embodiment will be explained. By placing the object, such as the rotary encoder 1a, to be orthogonal to the placement shown in FIG. 21, it becomes possible to set the shear direction for comparison based on the interference at right angles with the direction of pattern array. In this case, the shear value controller 153a in the inspection apparatus shown in FIG. 21 is replaced with a shear direction controller, and the shear direction is adjusted in place of the shear value for initialization. As an effectiveness of this modified embodiment, a more simple interference optical system which does not need the adjustment of shear value can be accomplished.

Next, the second variant embodiment will be explained. Objects of inspection other than patterns arrayed in a specific direction, including concentric patterns, patterns arrayed at a constant angular interval, multi-layer patterns, and three-dimensional patterns can be compared in optical manner through the disposition of the interference optical system 3 to have a radial displacement, angular displacement, focal position (depth direction) displacement, or the combination of the focal displacement and lateral displacement. As an effectiveness of this modified embodiment, objects for which the interference is rendered by any of the various interference optical systems can be inspected based on the optical comparison.

Figure 23:
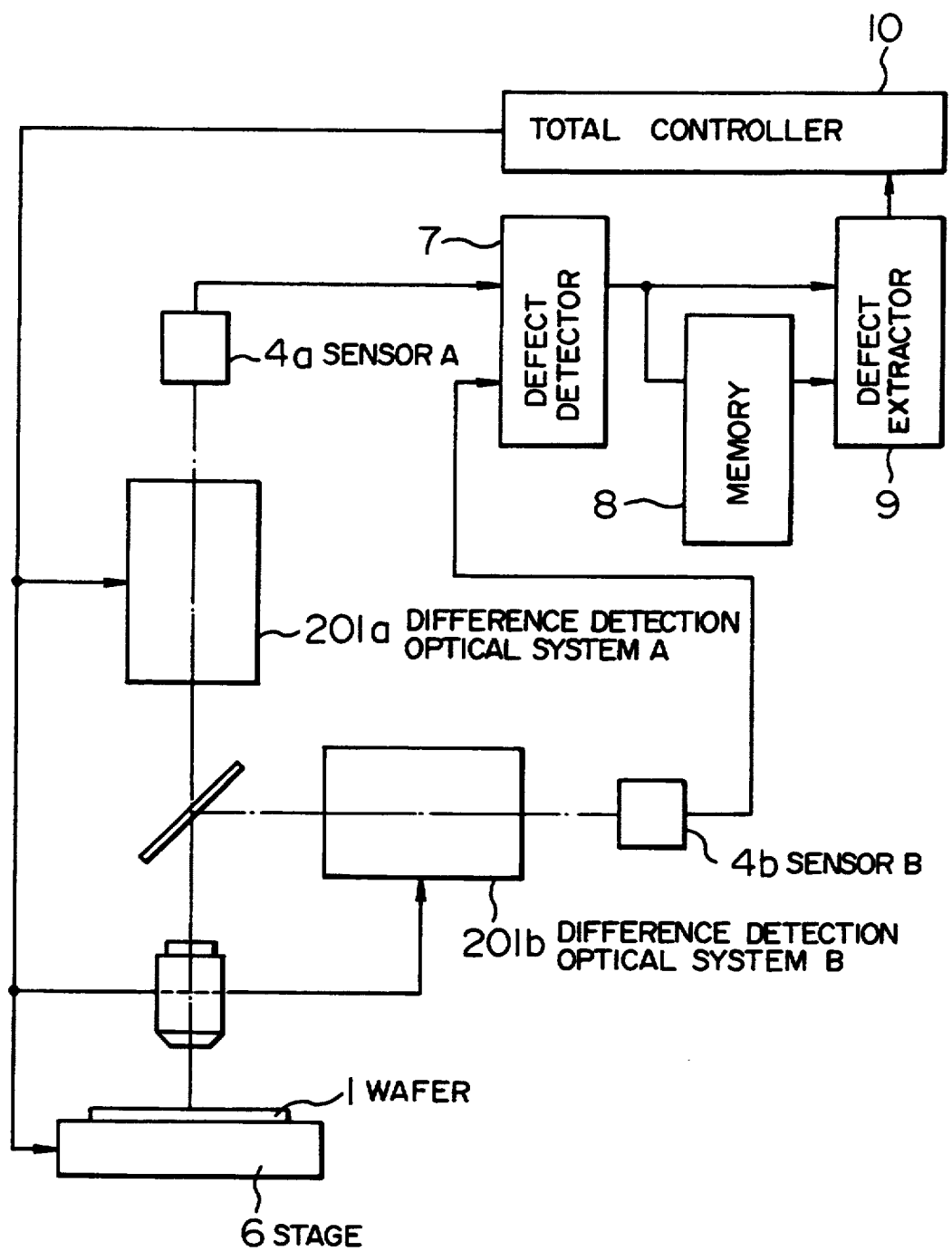
FIG. 23 is a block diagram of the pattern detection apparatus based on the fifth embodiment of this invention.
Figure 24:
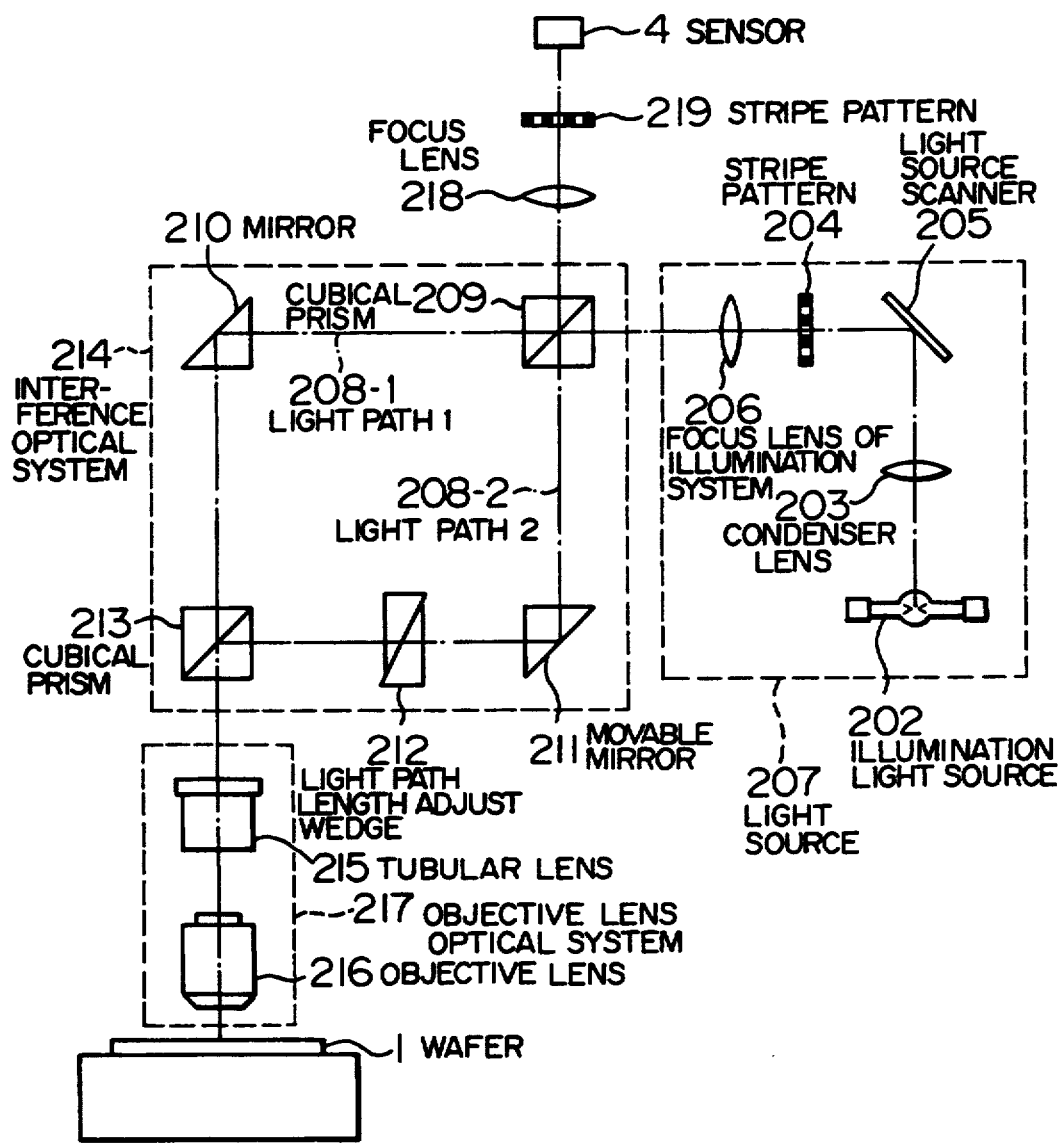
FIG. 24 is a block diagram showing the arrangement of the interference optical system used in the fifth embodiment of the pattern detection apparatus.

Next, the pattern detection apparatus based on the fifth embodiment of this invention will be explained with reference to FIG. 23 and FIG. 24. FIG. 23 shows the overall arrangement of the inspection apparatus, and FIG. 24 shows the optical system of difference detection.

The inspection apparatus consists of a stage 6 which positions a wafer (object of inspection) 1, an optical system (A) 201a which implements the difference detection for portions 11 and 12 of the wafer (see FIG. 5B), a sensor (A) 4a, an optical system (B) 201b which implements the difference detection for portions 11 and 13 of the wafer, a sensor (B) 4b, a defect detector 7 which detects a defective pattern based on the signals provided by the sensors (A, B), a memory 8 which stores defective patterns detected by the defect detector 7, a defect extractor 9 which detects a true defective pattern by comparing the detected defective pattern with the defective pattern of the preceding chip stored in the memory thereby to extract a defect, and a total controller 10 which controls all components including the stage 6, illumination optical system 2, image rotation means 52 and interference optical system (B) 3b.

The optical systems 201a and 201b for difference detection include of a light source section 207 including an illumination light source 202 which produces the light having a narrow wavelength band for illuminating the wafer, a condenser lens 203, a stripe pattern 204 which shapes the illumination light beam, a light source scanner 205, and an illumination focus lens 206; The optical systems 201a and 210b also include an interference optical system 214 including a cubical prism 209 which splits the illumination light beam along light paths (1, 2) 208-1 and 208-2, a mirror 210 which reflects the illumination light beam passing through the light path (1), a movable mirror 211 which reflects the illumination light beam passing through the light path (2), a combination wedge 212 which adjusts the relative lengths of the light path (1) and light path (2) to maintain a difference of $\pi$, a cubical prism 213 which merges the split illumination light beams; The apparatus further includes objective lens optical system 217 including tubular lens 215 and objective lens 216, a focus lens 218 which focuses the reflected light beam from the object lens optical system 217 through the interference optical system 214 so that it is detected by the sensors (A, B), and a stripe pattern 219.

These functional components operate to detect a small pattern defect as follows. Initially, as an initializing operation, the shear values dx and dy in the x and y directions of the wafer coordinate system are set equal to the cell pitches in the x and y directions by a means which was be explained before. Next, the stage 6 is positioned as shown in FIG. 5. The sensors (A, B) detect pattern differences, and the defect detector 7 detects a defect by determining the smaller of the two pattern signals of sensors A and B to be a defective pattern and stores it in the memory 8. Another defective pattern is detected at the same portion of the adjacent chip, and the defect extractor 9 compares it with the stored defective pattern thereby to extract a portion with a non-zero value, where it is zero in the stored defective pattern, as a true defect. Following the judgement of defect, the detected defective pattern is stored in the memory 8, and the same operation takes place for the next chip. On completion of defect judgement on one object chip, the stage is positioned to another section of the wafer and the defect judgement is repeated.

Next, the operation of the difference detection optical system will be explained. As an initializing operation of the interference optical system 214, the movable mirror 211 and combination wedge 212 are operated so that the two light paths have a difference of length of $\pi$ and the shear value in terms of the wafer pattern is equal to the intended cell pitch. The movable mirror 211 adjusts the shear value through the parallel movement, and the combination wedge 212 adjusts the light path length through the slide movement. The movable mirror and combination wedge are set to the designed values, and the stage is moved so that a portion without pattern and a memory cell section are within the view field. First, the wedge is adjusted for the portion without pattern so that the sensor (A) (or sensor (B) for the adjustment of the difference detection optical system (B)) produces a minimum output, and the sensor output is recorded for the memory cell section. Next, the movable mirror is moved along the light path, and the wedge is adjusted for the portion without pattern so that the sensor (A) produces a minimum output, and the sensor output is recorded for the memory cell section. These operations are repeated so that the output of the sensor (A) 4a for the memory cell section becomes minimum.

Figure 25:
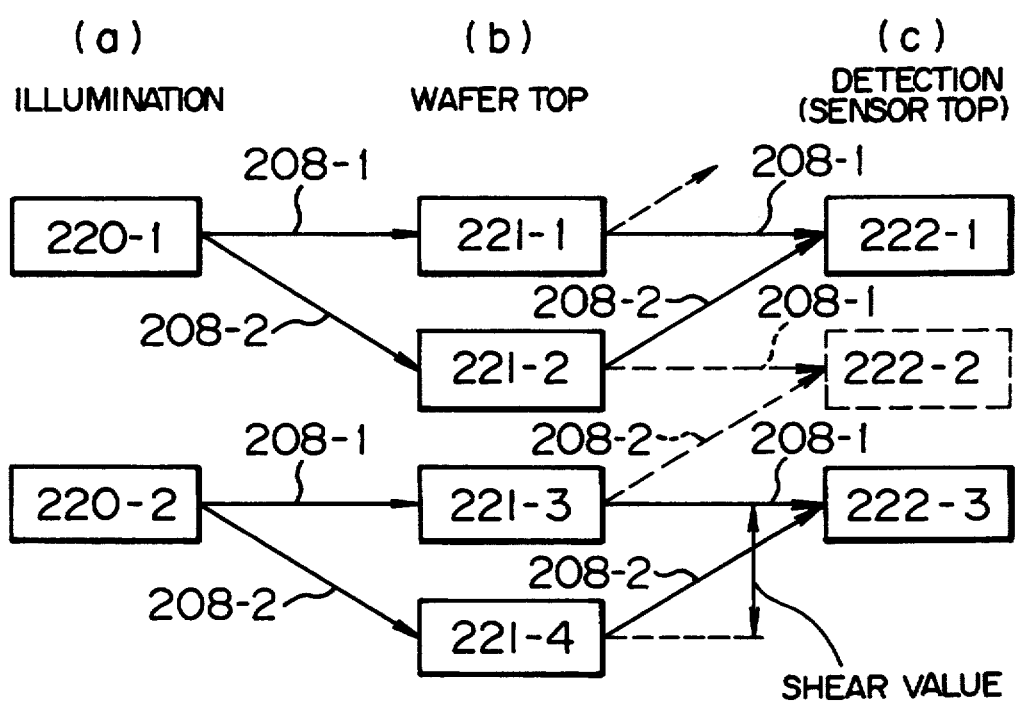
FIG. 25 is a diagram showing the state of illumination of the apparatus shown in FIG. 23, in which shown by (a) is the state of the illumination device, (b) is the state on the wafer, and (c) is the state of the detector (sensor A and sensor B)

Next, the functions of the stripe patterns 204 and 219 will be explained with reference to FIG. 25. The light beam from the light source 202 is shaped by the stripe pattern 204, and it illuminates only portions 220-1 and 220-2 of FIG. 25A. By setting the width of opening of the stripe pattern smaller than the shear value in terms of the wafer pattern, the wafer is illuminated as shown at (b) in FIG. 25. Indicated by 221-1 is a region which is illuminated by the light 220-1 through a light path 208-1, indicated by 221-2 is a region illuminated by the light 220-1 through a light path 208-2, indicated by 221-3 is a region illuminated by the light 220-2 through the light path 208-1, and indicated by 221-4 is a region illuminated by the 220-2 through the light path 208-2. These regions are detected by the sensors through the light paths 208-1 and 208-2 as shown at (c) in FIG. 25. Transmitting the light of only regions 222-1 and 222-3 (the same conductive regions of the illumination stripe pattern 204) for the sensor merges the light components of the same light source, and the interference can be induced. Through the scanning of the image of the light source by the light source scanner 205 at a time interval shorter than the storing time of the sensors (A, B) 4, the difference detection can be done uniformly for the entire view field of the optical system.

This embodiment provides the following effectiveness.

(1) The result of comparison of two cells in a chip pattern on a wafer is compared with the comparison result of another chip, and a defect is detected through the comparison of the two cells instead of using design data, although sections of a chip where two cell cannot be compared cannot be inspected.

(2) The interference optical system (split, phase shift and merge optical system) does not use the polarization, and therefore the detection is not influenced by the polarization of the object.

(3) The shear value is corrected at the time of initialization, and therefore the apparatus is readily responsive to objects of different cell pitches.

(4) Through the selection of the smaller of the results of two-cell comparison in the x and y directions, a true defect can be detected in sections where two cells can be compared.

Consequently, the automatic inspection of defects is possible for pattern sections of a wafer where two cells can be compared.

Next, the first variant embodiment will be explained. A zoom lens is used for the tubular lens 215, and the light path length adjusting wedge 212 is fixed or it is set to meet the cubical prism 209 or 213. The shear value is adjusted by varying the magnification factor of the zoom lens and the light path length is adjusted by the movable mirror 211. Once the light path length is set at the initializing operation, it does not vary when the shear value is varied, eliminating the need of recurrent light path length adjustment, and the operation is simplified.

Next, the second variant embodiment will be explained. This modified embodiment eliminates the light source scanner 205. The fluctuation of light intensity is evaluated in advance and it is corrected by means of a program or an electric circuit. This modified embodiment simplifies the operational procedure.

Next, the third variant embodiment will be explained. The stripe patterns 2-04 and 219 can be slits, spots or an array of spots.

Figure 26:
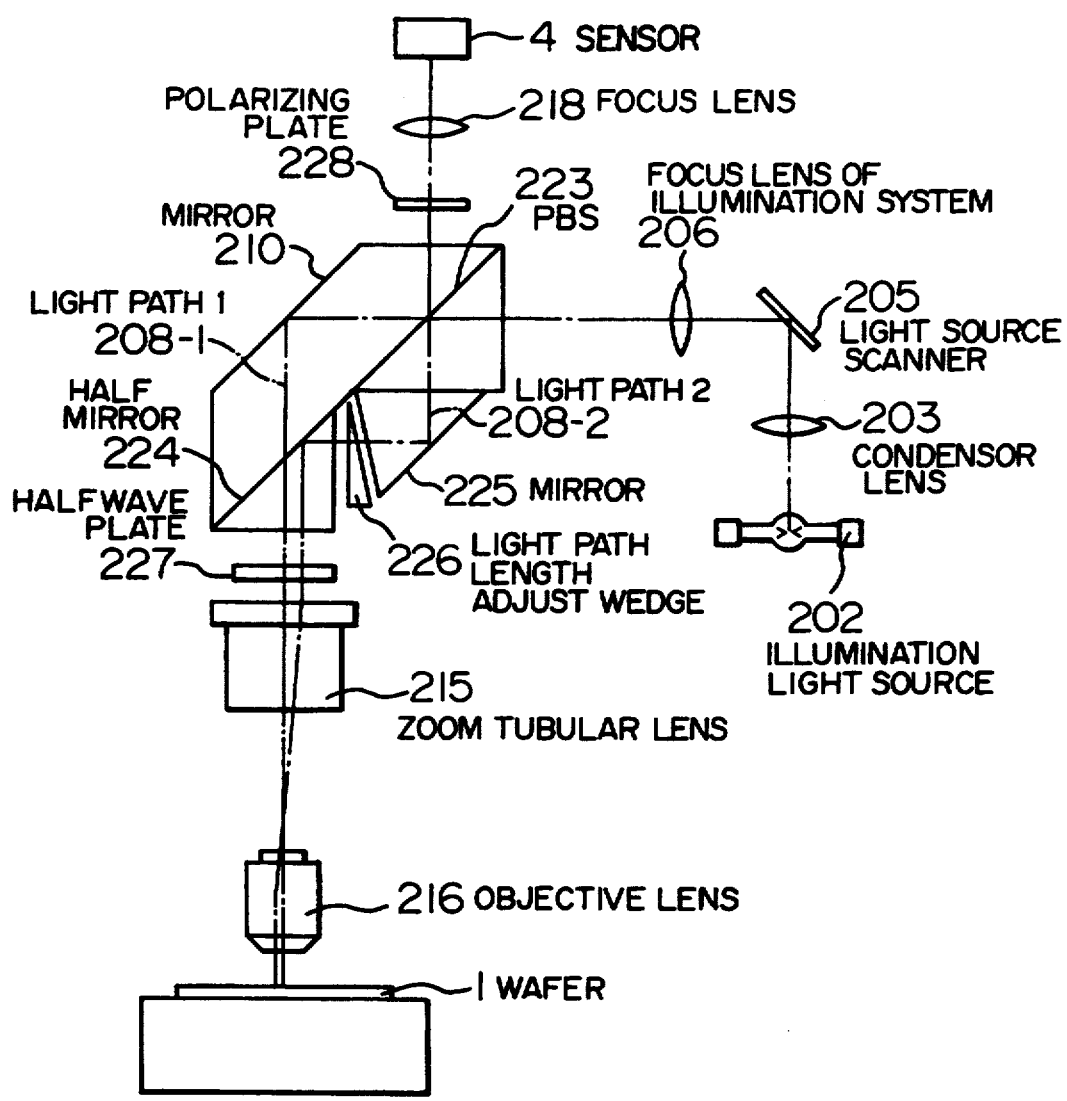
FIG. 26 is a block diagram showing a third variant embodiment of the interference optical system used in the embodiment shown in FIG. 24.

Next, the fourth variant embodiment will be explained. The optical system is arranged as shown in FIG. 26. The optical system consists of an illumination light source 202 which illuminates a wafer 1, a condenser lens 203, a light source scanner 205, an illumination light focus lens 206, a PBS 223 which splits the illumination light into a P polarization component on a light path (1) 208-1 and a S polarization component on a light path (2) 208-2, a mirror 210 which reflects the split illumination light on the light path (1), a mirror 225 which reflects the split illumination light on the light path (2), light path length adjusting combination wedge 226 which maintains the lengths of the light paths (1, 2) to have a difference of $\pi$, a half mirror 224 which merges the split illumination lights, a quarter wavelength plate 227, a zoom tubular lens 215, an objective lens 216, a focus lens 218 which focuses the reflected light so that it is detected by the sensors (A, B) 4a and 4b, and a polarizing plate 228.

The operation of the difference detection optical system will be explained. The illumination light beam is split by the PBS 223 into a transmitted P polarization component on the light path (1) and a reflected S polarization component on the light path (2). After both light beams are merged by the half mirror 224, the light beam is converted into a clockwise circular polarized ray and a counterclockwise polarized ray by the quarter wavelength plate 227. The reflected light from the object wafer 1 goes through the quarter wavelength plate 227 and becomes a S polarization light on the light path (1) and a P polarization light on the light path (2). Consequently, the light beam which goes through the PBS 223 and enters the sensor (A) consists of the S polarization light by way of the light path (1) and the P polarization light by way of the light path (2), and therefore the light beam which is used for illumination by way of the light path (1) and reflected goes through the light path (1), and the light beam which is used for illumination by way of the light path (2) and reflected goes through the light path (2). The light beams detected by the sensor have originated from a single point of the light source. These light components interfere, with their polarizing plane being rectified by the polarizing plate 228.

This modified embodiment eliminates the need of masking, and the entire detection view field can be used.

This invention enables the detection of small defects and the measurement of the pattern pitch of a repetitive pattern based on the optical interference (optical split, phase shift and merge). Particularly, when the inventive method and apparatus are applied to the inspection of repetitive patterns such as wafer patterns, small defects can be detected without deteriorating the detection speed through the adoption of a detection pixel size larger than the size of small defects, while retaining the resolution which enables the detection of small defects.

We claim:

1. A pattern detection method for detecting or observing a repetitive pattern on an object, said method comprising illuminating the object with coherent or partially coherent light; detecting reflected or transmitted light from the object to produce a detected optical image; splitting the detected optical image provide first and second optical images; merging the first and second optical while shifting the relative phase of said first and second optical images by 180° to produce a combined optical image; and detecting or observing pattern information in said combined optical image.

2. A pattern detection method according to claim 1, wherein said pattern information is information indicative of a defect in one of said first and said second patterns.

3. For use with a pattern which is repetitive in x and y directions, a pattern detection method comprising the steps of:
- splitting an optical image of the pattern in the x direction into a first plurality of optical images;
- merging said first plurality of optical images, while shifting the relative phase of the first plurality of optical images by an amount dependent upon the repetitiveness in the x direction of the repetitive pattern, to produce a first merged optical image;
- detecting the first merged optical image with a first opto-electric transducer to produce a first electrical signal indicative of the first merged optical image;
- splitting an optical image of the pattern in the y direction into a second plurality of optical images;
- merging said second plurality of optical images while shifting the relative phase of the second plurality of optical images by an amount dependent on the repetitiveness in the y direction of the repetitive pattern to produce a second merged optical image;
- detecting the second merged optical image with a second opto-electric transducer to produce a second electrical signal indicative of the second merged optical image; and
- detecting pattern information based on the first and second electrical signals.

4. A pattern detection apparatus for detecting repetitive pattern on an object, said apparatus comprising an illumination optical system for illuminating the object with a coherent or partially coherent light; a detection optical system for detecting reflected or transmitted light from the object to produce a detected optical image; an optical splitting system for splitting the detected optical image into first and second optical images; a merging optical system for merging said first and second optical images, while shifting the relative phase of said first and second optical images by 180°; and means for detecting or observing pattern information in the merged optical image.

5. A pattern detection apparatus according to claim 4, wherein said merging optical system includes a zoom relay lens, an adjustable multi-refraction device, half mirror, lens, diffraction grating, or Fresnel zone plate.

6. A pattern detection apparatus according to claim 4, wherein said illumination optical system includes means for reducing the plane wave or the displacement from the plane wave to a value smaller than the wavelength on the pattern.

7. A pattern detection apparatus for detecting a repetitive pattern in an object, said apparatus comprising an illumination light source for illuminating the object with a coherent or partially coherent light; a first detection optical system for detecting reflected or transmitted light in a first optical path from the object to produce a first detected optical image; a second detection optical system for detecting reflected or transmitted light in a second optical path from the object to produce a second detected optical image; a merging optical system for merging the first and second optical images while shifting the relative phase between said first and second optical images by 180° to provide a merged optical image; and means for detecting or observing pattern information in the merged optical image.

* * * * *